US007569385B2

(12) United States Patent
Haas

(10) Patent No.: US 7,569,385 B2
(45) Date of Patent: Aug. 4, 2009

(54) MULTIPOTENT AMNIOTIC FETAL STEM CELLS

(75) Inventor: Martin Haas, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 193 days.

(21) Appl. No.: 10/918,739

(22) Filed: Aug. 13, 2004

(65) Prior Publication Data

US 2005/0054093 A1 Mar. 10, 2005

Related U.S. Application Data

(60) Provisional application No. 60/495,513, filed on Aug. 14, 2003, provisional application No. 60/495,437, filed on Aug. 14, 2003.

(51) Int. Cl.
*C12N 5/00* (2006.01)
*C12N 5/06* (2006.01)
*C12N 5/10* (2006.01)
(52) U.S. Cl. .................. 435/325; 435/402; 435/455
(58) Field of Classification Search .............. 435/325, 435/402, 455
See application file for complete search history.

(56) References Cited

U.S. PATENT DOCUMENTS

| 4,714,680 | A | 12/1987 | Civin |
| 5,061,620 | A | 10/1991 | Tsukamoto et al. |
| 5,087,570 | A | 2/1992 | Weissman et al. |
| 5,486,359 | A | 1/1996 | Caplan et al. |
| 5,556,783 | A | 9/1996 | Lavker et al. |
| 5,670,372 | A | 9/1997 | Hogan |
| 5,827,740 | A | 10/1998 | Pittenger |
| 6,200,806 | B1 | 3/2001 | Thomson |
| 6,432,711 | B1 | 8/2002 | Dinsmore et al. |
| 6,506,574 | B1 | 1/2003 | Rambhatla et al. |
| 6,670,124 | B1 | 12/2003 | Chow et al. |
| 2003/0215942 | A1 | 11/2003 | Chow et al. |
| 2005/0042595 | A1 | 2/2005 | Haas |
| 2005/0123521 | A1* | 6/2005 | Zern et al. ............. 424/93.21 |
| 2005/0124003 | A1* | 6/2005 | Atala et al. ............. 435/7.2 |

FOREIGN PATENT DOCUMENTS

| EP | 0 647 267 B1 | 8/2000 |
| WO | WO 01/23532 A1 | 4/2001 |
| WO | WO 03/042405 * | 5/2003 |
| WO | WO 03/042405 A2 | 5/2003 |

OTHER PUBLICATIONS

Carotta, et al. 2004. Directed differentiation and mass cultivation of pure erythroid progenitors from mouse embryonic stem cells. *Blood*, 104(6):1873-1880.
Chambers, et al. 2003. Functional expression cloning of Nanog, a pluripotency sustaining factor in embryonic stem cells. *Cell*, 113:643-655.
Deutsch, et al. 2001. A bipotential precursor population for pancreas and liver within the embryonic endoderm. *Development*, 128:871-881.
Donovan, et al. 2001. The end of the beginning for pluripotent stem cells. *Nature*, 414:92-97.
Draper, et al. 2002. Surface antigens of human embryonic stem cells: Changes upon differentiation in culture. *Journal of Anatomy*, 200:249-258.
Erlich, et al. 1991. HLA-DR, DQ and DP typing using PCR amplification and immobilized probes. *European Journal of Immunogenetics*, 18:33-55.
Fraichard, et al. 1995. In vitro differentiation of embryonic stem cells into glial cells and functional neurons. *Journal of Cell Science*, 108:3181-3188.
Fuchs, et al. 2004. Diaphragmatic reconstruction with autologous tendon engineered from mesenchymal amniocytes. *Journal of Pediatric Surgery*, 39(6):834-838.
Gronthos, et al. 2001. Surface protein characterization of human adipose tissue-derived stromal cells. *Journal of Cellular Physiology*, 189:54-63.
Henderson, et al. 2002. Preimplantation human embryos and embryonic stem cells show comparable expression of stage-specific embryonic antigens. *Stem Cells*, 20:329-337.
Jaiswal, et al. 1997. Osteogenic differentiation of purified, culture-expanded human mesenchymal stem cells in vitro, *Journal of Cellular Biochemistry*, 64:295-312.
Itskovitz-Eldor, et al. 2000. Differentiation of human embryonic stem cells into embryoid bodies comprising the three embryonic germ layers. *Molecular Medicine*, 6(2):88-95.
Kawasaki, et al. 1993. Genetic analysis using polymerase chain reaction-amplified DNA and immobilized oligonucleotide probes: Reverse dot-blot typing. *Methods in Enzymology*, 218:369-381.
Kim, et al. 2002. Dopamine neurons derived from embryonic stem cells function in an animal model of Parkinson's disease. *Nature*, 418:50-56.
Kögler, et al. 2004. A new human somatic stem cell from placental cord blood with intrinsic pluripotent differentiation potential. *The Journal of Experimental Medicine*, 200(2):123-135.
Lee, et al. 2000. Efficient generation of midbrain and hindbrain neurons from mouse embryonic stem cells. *Nature Biotechnology*, 18:675-679.

(Continued)

*Primary Examiner*—Anne Marie S Wehbe
(74) *Attorney, Agent, or Firm*—Knobbe Martens Olson & Bear LLP

(57) ABSTRACT

A source of multipotent amniotic fluid/fetal stem cells (MAFSCs) is disclosed. MAFSC are of fetal origin and have a normal diploid karyotype. These cells are characterized by the following cell surface markers: SSEA3, SSEA4, Tra-1-60, Tra-1-81, Tra-2-54, HLA class I, CD13, CD44, CD49b, CD105 and are distinguished by the absence of the antigen markers CD34, CD45, and HLA Class II, but are distinguished from mouse embryonic stem cells in that these cells do not express the cell surface marker SSEA1. MAFSC express the stem cell transcription factor Oct-4. MAFSC cells can be propagated for an indefinite period of time in continuous culture in an undifferentiated state. The MAFSCs have the ability to differentiate in culture in a regulated manner, into three or more subphenotypes. Cells can then be differentiated into endodermal, mesodermal and ectodermal derived tissues in vitro and in vivo. A method for isolating, identifying, expanding and differentiating MAFSCs is disclosed.

12 Claims, 6 Drawing Sheets

OTHER PUBLICATIONS

Liu, et al. 2000. Embryonic stem cells differentiate into oligodendrocytes and myelinate in culture and after spinal cord transplantation. *Proc. Natl. Acad. Sci. USA*, 97(11):6126-6131.

Lodie, et al. 2002. Systematic analysis of reportedly distinct populations of multipotent bone marrow-derived stem cells reveals a lack of distinction. *Tissue Engineering*, 8(5):739-753.

Lumelsky, et al. 2001. Differentiation of embryonic stem cells to insulin-secreting structures similar to pancreatic islets. *Science*, 292:1389-1394.

Maltsev, et al. 1993. Embryonic stem cells differentiate in vitro into cardiomyocytes representing sinusnodal, atrial and ventricular cell types. *Mechanisms of Development*, 44:41-50.

Marshall, et al. 2001. Isolation and maintenance of primate embryonic stem cells. *Methods in Molecular Biology*, 158:11-18.

McKay, R. 1997. Stem cells in the central nervous system. *Science*, 276:66-71.

McKay, R. 2000. Stem cells—hype and hope. *Nature*, 406:361-364.

Mitsui, et al. 2003. The homeoprotein Nanog is required for maintenance of pluripotency in mouse epiblast and ES cells. *Cell*, 113:631-642.

Odorico, et al. 2001. Multilineage differentiation from human embryonic stem cell lines. *Stem Cells*, 19:193-204.

Olerup, et al. 1992. HLA-DR typing by PCR amplification with sequence-specific primers (PCR-SSP) in 2 hours: An alternative to serological DR typing in clinical practice including donor-recipient matching in cadaveric transplantation. *Tissue Antigens*, 39:225-235.

Pittenger, et al. 1999. Multilineage potential of adult human mesenchymal stem cells. *Science*, 284:143-147.

Pittinger, et al. 2001. Mesenchymal stem cells of human adult bone marrow. In D. R. Marshak, et al. (Eds.), *Stem Cell Biology*, (pp. 349-373). Cold Spring Harbor, NY: Cold Spring Harbor Laboratory Press.

Potocnik, et al. 1994. In vitro generation of lymphoid precursors from embryonic stem cells. *The EMBO Journal*, 13(22):5274-5283.

Prusa, et al. 2002. Amniotic fluid cells and human stem cell research—A new connection. *Med Sci Monit*, 8(11):RA253-257.

Prusa, et al. 2003. Oct-4-expressing cells in human amniotic fluid: A new source for stem cell research. *Human Reproduction*, 18(7):1489-1493.

Rathjen, et al. 1998. Properties and uses of embryonic stem cells: Prospects for application to human biology and gene therapy. *Reprod. Fertil. Dev.*, 10:31-47.

Reid, L. M. 1990. Stem cell biology, hormone/matrix synergies and liver differentiation. *Current Opinion in Cell Biology*, 2:121-130.

Reubinoff, et al. 2000. Embryonic stem cell lines from human blastocysts: Somatic differentiation in vitro. *Nature Biotechnology*, 18:399-404.

Robertson, E. J. (Ed.) 1987. *Teratocarcinomas and embryonic stem cells: A practical approach.* Washington, D.C.: IRL Press.

Saiki, et al. 1989. Genetic analysis of amplified DNA with immobilized sequence-specific oligonucleotide probes. *Proc. Natl. Acad. Sci.*, USA, 86:6230-6234.

Schuldiner, et al. 2000. Effects of eight growth factors on the differentiation of cells derived from human embryonic stem cells. *Proc. Natl. Acad. Sci. USA*, 97(21):11307-11312.

Shamblott, et al. 1998 Derivation of pluripotent stem cells from cultured human primordial germ cells. *Proc. Natl. Acad. Sci. USA*, 95:13726-13731.

Sherley, J. L. 2002. Asymmetric cell kinetics genes: The key to expansion of adult stem cells in culture. *Stem Cells*, 20:561-572.

Shihabuddin, et al. 1999. The search for neural progenitor cells: Prospects for the therapy of neurodegenerative disease. *Molecular Medicine Today*, 5:474-480.

Terasaki, et al. 1964. Microdroplet assay of human serum cytotoxins. *Nature*, 204:998-1000.

Thomson, et al. 1995. Isolation of a primate embryonic stem cell line. *Proc. Natl. Acad. Sci. USA*, 92:7844-7848.

Thomson, et al. 1998. Embryonic stem cell lines derived from human blastocysts. *Science*, 282:1145-1147.

Tiercy, et al. 1990. A new approach for the analysis of HLA class II polymorphism: 'HLA oligotyping.' *Blood Reviews*, 4:9-15.

Toma, et al. 2001. Isolation of multipotent adult stem cells from the dermis of mammalian skin. *Nature Cell Biology*, 3:778-784.

Tsai, et al. 2004. Isolation of human multipotent mesenchymal stem cells from second-trimester amniotic fluid using a novel two-stage culture protocol. *Human Reproduction*, 19(6):1450-1456.

Uchida, et al. 2000. Direct isolation of human central nervous system stem cells. *PNAS*, 97(26):14720-14725.

Vogel, G. (2002). Can adult stem cells suffice?*Science*, 292:1820-1822.

Vogel, G. (2002). An embryonic alternative. *Science*, 292:1822.

Wassarman, P. M., and M. L. DePamphilis, Eds. 1993. *Methods in enzymology: Guide to techniques in mouse development.* vol. 225. San Diego: Academic Press.

Wichterle, et al. 2002. Directed differentiation of embryonic stem cells into motor neurons. *Cell*, 110:385-397.

Wiles, M. V. 1993. Embryonic stem cell differentiation in vitro. *Methods in Enzymology*, 225:900-918.

Yoo, et al. 1998. The chondrogenic potential of human bone-marrow-derived mesenchymal progenitor cells. *The Journal of Bone and Joint Surgery, Incorporated.* 80-A(12):1745-1757.

*Diseases Treatable by Stem Cell Transplant.* (n.d.). Retrieved Nov. 8, 2004, from http://www.marrow.org/MEDICAL/diseases_treatable_by_stem_cell_transplants.html.

GenBank Accession No. NM_003219, dated Oct. 26, 2004.

De Coppi, et al., "Isolation of amniotic stem cell lines with potential for therapy", *Nature Biotechnology*, 2007, vol. 25, No. 1, pp. 100-106.

Delo, et al., "Amniotic Fluid and Placental Stem Cells", *Methods in Enzymology*, 2006, vol. 419, pp. 426-437.

Dominici, et al., "Minimal criteria for defining multipotent mesenchymal stromal cells. The International Society for Cellular Therapy position statement", *Cytotherapy*, 2006, vol. 8, No. 4, pp. 315-317.

Yen, et al., "Isolation of Multipotent Cells from Human Term Placenta", *Stem Cells*, 2005, vol. 23, pp. 3-9.

* cited by examiner

HLA Class II

CD34

CD117

Stro-1 negative control

SSEA3

SSEA4

Tra-2-54

CD45

Human Mesenchymal Cell Markers and Controls

MULTIPOTENT AMNIOTIC FETAL STEM CELLS

RELATED APPLICATIONS

This application claims priority under 35 U.S.C. §119 to U.S. Provisional Application No. 60/495,513, filed Aug. 14, 2003, and U.S. Provisional Application No. 60/495,437, filed Aug. 14, 2003 the disclosures of which are incorporated by reference herein in their entireties.

BACKGROUND OF THE INVENTION

1. Field of the Invention

The invention relates to the field of stem cell research, and more particularly to the isolation of stem cells from amniotic fluid. Stem cells derived from amniotic fluid can then be differentiated to many types of cells or tissues.

2. Description of the Related Art

Stem cells have the ability to divide for indefinite periods in culture and to give rise to specialized cells. Stem cells can give rise to many types of differentiated cells, and may be useful to treat many types of diseases. There are several types of stem cells, such as embryonic stem cells, which are undifferentiated cells from the embryo, and adult stem cells, which are undifferentiated cells derived from various mature tissues.

Embryonic stem cells have the potential to become a wide variety of specialized cell types. This ability of an embryonic stem cell to become a variety of cell types is termed "pluripotent." Embryonic stem cells can be differentiated into a host of cell types and tissue types, which can be used for basic research, drug discovery, treatment and prevention of diseases. For example, U.S. Pat. No. 6,506,574 to Rambhatla, which is incorporated by reference herein in its entirety, discloses methods of differentiating embryonic stem cell cultures into hepatocyte lineage cells. Other methods for the preparation of embryonic stem cells are disclosed, for example, in U.S. Pat. No. 6,200,806 to Thomson; U.S. Pat. No. 5,670,372 to Hogan, and U.S. Pat. No. 6,432,711 to Dinsmore, each of which is incorporated by reference herein in its entirety.

Human Embryonic Stem cells (hES) are derived from the inner cell mass of the blastocyst, the earliest stage of embryonic development of the fertilized egg. The blastocyst is a preimplantation stage of the embryo, a stage before the embryo would implant in the uterine wall. When cultured on an inactivated feeder layer of cells according to conditions described by Thompson and colleagues (Thomson, et al., (1995) *Proc. Natl. Acad. Sci. U.S.A.* 92:7844-7848; Thomson, et al. (1998) *Science* 282:1145-1147; Marshall, et al., (2001) *Methods Mol. Biol.* 158:11-18), each of which is incorporated by reference herein in its entirety, the inner layer cells of the blastocyst can be grown in vitro indefinitely in an undifferentiated state. Properly propagated hES cells have unlimited potential to double while maintaining their capacity of differentiating into the three layers of the embryo, Ectoderm (Ec), Mesoderm (Me) and Endoderm (En); they are pluripotent. When grown as pluripotent hES, the cells maintain a euploid karyotype and are not prone to senescence. hES cells have been differentiated in vitro into skin and brain (Ec), heart, muscle, kidney and blood (Me), and into pancreatic, thyroid and lung cells (En) (Fraichard, et al., (1995) *J. Cell Sci.* 108:3181-3188; Itskovitz-Eldor, et al., (2000). *Mol. Med.* 6:88-95; Lee, et al., (2000) *Nat. Biotechnol.* 18:675-679; Liu, et al., (2000) *Proc. Natl. Acad. Sci. U.S.A.* 97:6126-6131; Lumelsky, et al., (2001) *Science* 292:1389-1394; Maltsev, et al., (1993). *Mech. Dev.* 44:41-50; Odorico, et al., (2001) *Stem Cells* 19:193-204. Potocnik, et al., *EMBO. J.* 13:5274-5283; Reubinoff, et al., (2000) *Nat. Biotechnol.* 18:399-404; Schuldiner, et al., (2001) *Proc. Natl. Acad. Sci. USA* 97:1997: 11307-11312; Kim, et al., (2002) *Nature* 418:50-56; Wichterle, et al., (2002) *Cell* 110:385-397), each of which is incorporated by reference herein in its entirety.

Human embryonic stem cells display a distinct group of cell surface antigens, SSEA-3, SSEA-4, TRA-2-54 (alkaline phosphatase), TRA-1-60 and TRA-1-81, in addition to expressing specific transcription factors OCT-4, NANOG, SOX-2, FGF-4 and REX-1 (Henderson, et al., (2002) *Stem Cells* 20:329-337; Draper, et al., (2002). *J. Anat.* 200:249-258; Mitsui et al., (2003) *Cell* 113:631-642; Chambers et al., (2003) *Cell* 113:643-655), each of which is incorporated by reference herein in its entirety. Additionally, hES cells (i) are capable of symmetrical division in vitro without differentiating; (ii) can integrate into all fetal tissues during in vivo development; (iii) are capable of colonizing the germ line and give rise to egg or sperm cells; (iv) develop into teratocarcinomas in immunologically impaired adult mice—another measure of pluripotency, and lack the G1 checkpoint in the cell cycle like somatic cells but spend most of their time in S phase.

Stem cells can also be derived from nonembryonic sources. For example, an additional class of human stem cells are the mesenchymal or adult stem cells (MSC). Adult stem cells are undifferentiated, like embryonic stem cells, but are present in differentiated tissues. Adult stem cells are capable of differentiation into the cell types from the tissue that the adult stem cell originated. Adult stem cells (MSC) have been derived from the nervous system (McKay, R. (1997) *Science* 276:66-71. Shihabuddin, et al., (1999) *Mol. Med. Today* 5:474-480), bone marrow (Pittenger, et al., (1999) *Science* 284:143-147; Pittenger, M. F. and Marshak, D. R. (2001). In: Mesenchymal stem cells of human adult bone marrow. Marshak, D. R., Gardner, D. K., and Gottlieb, D. eds. (Cold Spring Harbor, N.Y.: Cold Spring Harbor Laboratory Press) 349-374); adipose tissue (Gronthos, et al., (2001) *J. Cell. Physiol.* 189:54-63), dermis (Toma, et al., (2001) *Nature cell Biol.* 3:778-784) and pancreas and liver (Deutsch, et al., (2001) *Development* 128:871-881, each of which is incorporated by reference herein in its entirety, and other organs.

Several patents disclose various aspects of adult stem cells. For example, U.S. Pat. No. 5,486,359 to Caplan, which is incorporated by reference herein in its entirety, discloses methods of isolating human mesenchymal stem cells, and U.S. Pat. No. 5,556,783 to Lavker, which is incorporated by reference herein in its entirety, discloses methods of culturing hair follicle stem cells. Examples of patents disclosing haematopoietic stem cells include U.S. Pat. No. 4,714,680 to Civin, U.S. Pat. No. 5,061,620 to Tsukamoto, and U.S. Pat. No. 5,087,570 to Weissman, each of which is incorporated by reference herein in its entirety.

The mesenchymal/adult stem cells (MSC—or MAP cells) express a variety of cell surface proteins such as CD9, CD10, CD13, CD49b in addition to other markers. MAP cells have the potential to differentiate into different mesenchymal tissues including bone, cartilage, fat, tendon, muscle and bone marrow stroma: they are multipotent but not pluripotent. MAP cells do not, as a rule, express the SSEA-3, SSEA-4, TRA-2-54, TRA-1-60 and TRA-1-81 markers expressed by hES cells. Although adult stem cells can be expanded in culture, they do not appear to be immortal (McKay R. (2000) *Nature* 406:61-364; Vogel G. (2002) *Science* 292:820-1822; Donovan and Gearhart J. (2001) *Nature* 414:2-97, each of which is incorporated by reference herein in its entirety). It has been proposed that the mortality of mesenchymal/adult stem cells is due to the asymmetric kinetics of adult stem cell expansion (Sherley, J. L. (2002) *Stem Cells* 20:61-572, which is incorporated by reference herein in its entirety).

Unfortunately, researchers have found that non-embryonic types of stem cells ("adult stem cells") are not as capable of differentiating into many different tissue types as are embryonic stem cells, so embryonic stem cells still have many advantages over the use of adult stem cells. However, one obstacle with the isolation of embryonic stem cells is that the cells are derived from embryos at the "blastocyst" stage. Human embryonic stem cell research is encumbered by an emotionally charged political and moral ethics debate and is likely to remain so for years to come.

Additionally, human embryonic stem cells (hES) have been found to be tumorigenic when injected into immunologically-impaired animals, i.e. in the context of post-natal tissues, whereas the MAP cells are not. The tumorigenic attributes of hES cells are not frequently addressed, though this issue may burden their use in replacement cell therapy in the future. The political, moral and ethical issues around hES cells and their tumorigenic properties, as well as the perceived difficulties of expanding undifferentiated adult stem cells in culture, while maintaining a genetically normal genome, are major barriers in the development of human cell replacement therapy.

To address the above-described obstacles, while still allowing research progress towards successful treatment of human diseases, methods of isolating novel sources of multipotent or pluripotent human stem cells that are not fraught by the ethical, tumorigenic, or mortality hurdles are needed.

SUMMARY OF THE INVENTION

Embodiments of the invention include a composition having multipotent or pluripotent stem cells derived from amniotic fluid. The cells may be undifferentiated, or they may also be differentiated cells derived from the above-described multipotent or pluripotent stem cells. The cells may be administered to a patient as a method of gene therapy, by administering genetically modified multipotent or pluripotent cells of the invention. Further, in some embodiments, the cells may be characterized by expressing the following markers: SSEA3, SSEA4, Tra1-60, Tra1-81, Tra2-54, and Oct-4, but do not express the cell surface marker SSEA1. In additional embodiments, the cells can be further characterized by the expression of the markers HLA class I, CD13, CD44, CD49b, and CD105.

Additional embodiments of the invention provide methods of preparing multipotent or pluripotent stem cells, by harvesting amniotic fluid and isolating stem cells from the fluid. If desired, the method may involve additional steps of centrifugation, plating onto a medium, and proliferation of the cells.

Further embodiments of the invention include methods of preparing multipotent or pluripotent stem cells, by isolating the stem cells from amniotic fluid, purifying the stem cells, and growing the stem cells in or on a medium.

Yet another embodiment of the invention provides a method of preparing differentiated cells by harvesting amniotic fluid, isolating stem cells from the amniotic fluid, culturing the isolated stem cells, and differentiating the stem cells into desired cell types. The differentiated cells can have a biological tissue type, or a desired cell type, such as hematopoietic cell, a neuronal cell, an endodermal cell, an ectodermal cell, or a mesodermal cell.

Additional embodiments include a multipotent or pluripotent cell derived from amniotic fluid which has been genetically modified. For example, the cell may be genetically modified to express TERT. Further embodiments of the invention include methods of gene therapy treatment of a patient, by administering genetically modified multipotent or pluripotent cells.

Further embodiments of the invention include methods of promoting bone marrow regeneration in an animal by transplanting MAFSCs or their derivatives into the bone marrow of the animal.

Further embodiments of the invention includes multipotent stem cells isolated from amniotic fluid, characterized by a) the ability to grow in continuous culture for at least 60 generations, and b) the presence of at least one, or at least two, or at least three, or at least four, or at least five, or at least six, or all of the markers selected from the following group: SSEA3, SSEA4, Tra-1-60, Tra-1-81, Tra-2-54, and Oct-4.

Additional embodiments include a multipotent stem cell isolated from amniotic fluid, characterized by a) the ability to grow in continuous culture for at least 60 generations, and b) the presence of the marker SSEA3. Additional embodiments include a multipotent stem cell isolated from amniotic fluid, characterized by a) the ability to grow in continuous culture for at least 60 generations, and b) the presence of the marker SSEA4.

Additional embodiments include a multipotent stem cell isolated from amniotic fluid, characterized by a) the ability to grow in continuous culture for at least 60 generations, and b) the presence of the marker TRA1-60. Additional embodiments include a multipotent stem cell isolated from amniotic fluid, characterized by a) the ability to grow in continuous culture for at least 60 generations, and b) the presence of the marker TRA1-81. Additional embodiments include a multipotent stem cell isolated from amniotic fluid, characterized by a) the ability to grow in continuous culture for at least 60 generations, and b) the presence of the marker TRA2-54. Additional embodiments include a multipotent stem cell isolated from amniotic fluid, characterized by a) the ability to grow in continuous culture for at least 60 generations, and b) the presence of the transcription factor OCT-4. In additional embodiments, the above multipotent stem cells can also be characterized by expressing at least one marker selected from the group consisting of: HLA Class I, CD13, CD44, CD49b, and CD105.

Yet further embodiments of the invention includes pluripotent stem cells isolated from amniotic fluid, characterized by a) the ability to grow in continuous culture for at least 60 generations, and b) the presence of at least one, or at least two, or at least three, or at least four, or at least five, or all of the markers selected from the following group: SSEA3, SSEA4, Tra-1-60, Tra-1-81, Tra-2-54, and Oct-4. In further embodiments, the above stems can be further characterized by expressing at least one marker selected from the group consisting of: HLA Class I, CD13, CD44, CD49b, and CD105.

Additional embodiments include a pluripotent stem cell isolated from amniotic fluid, characterized by a) the ability to grow in continuous culture for at least 60 generations, and b) the presence of the marker SSEA3. Additional embodiments include a pluripotent stem cell isolated from amniotic fluid, characterized by a) the ability to grow in continuous culture for at least 60 generations, and b) the presence of the marker SSEA4. Additional embodiments include a pluripotent stem cell isolated from amniotic fluid, characterized by a) the ability to grow in continuous culture for at least 60 generations, and b) the presence of the marker TRA1-60. Additional embodiments include a pluripotent stem cell isolated from amniotic fluid, characterized by a) the ability to grow in continuous culture for at least 60 generations, and b) the presence of the marker TRA1-81. Additional embodiments include a pluripotent stem cell isolated from amniotic fluid, characterized by a) the ability to grow in continuous culture for at least 60 generations, and b) the presence of the marker TRA2-54. Additional embodiments include a pluripotent stem cell isolated from amniotic fluid, characterized by a) the ability to grow in continuous culture for at least 60 generations, and b) the presence of the transcription factor OCT-4. In further embodiments, the above pluripotent stem cells can be further characterized by expressing at least one marker selected from the group consisting of: HLA Class I, CD13, CD44, CD49b, and CD105.

BRIEF DESCRIPTION OF THE DRAWINGS

FIG. 2 shows additional images of cells derived from amniotic fluid.

DETAILED DESCRIPTION OF THE PREFERRED EMBODIMENT

Figure 1A:
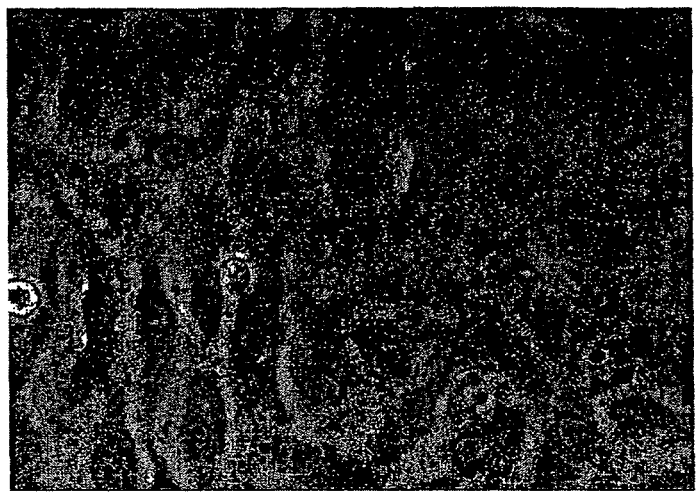
FIG. 1 shows three microscopic images of cultures derived from amniotic fluid. The photograph in FIG. 1A illustrates cells having an "epithelial" like morphology.
FIGS. 1B and 1C show cell cultures having a fibroblastic morphology.

A newly discovered source of human stem cells is described herein. The cells, coined Multipotent Amniotic Fetal Stem Cells (MAFSC), are immortal in culture, maintain euploidy for >1 year in culture, share markers with human ES cells, and are capable of differentiating into all three germ layers of the developing embryo, Endoderm, Mesoderm and Ectoderm. These human stem cells are found in the amnion harvested during the second trimester of human pregnancies.

While amniotic fluid contains multiple morphologically-distinguishable cell types, the majority of the cells are prone to senescence and are lost from cultures grown under MAFSC culture conditions. More than 80% of amniotic fluid harvests from normal 16-18 week pregnancies give rise to continuous MAFSC lines. The MAFSCs may be harvested from amniotic fluid from pregnant females at any stage in the gestation period.

MAFSC are of fetal origin, and have a normal diploid karyotype. Additionally, MAFSC cells are devoid of tumorgenic properties: unlike hEC cells, human MAFSC cells do not grow into teratocarcinomas when injected into SCID mice. This property may be especially useful in using MAFSC cells or their derivatives for human gene therapy purposes.

The MAFSC cells of the invention have been shown to be multipotent, as several main cell types have been derived from them. As used herein, the term "multipotent" refers to the ability of MAFSC to differentiate into several main cell types. The MAFSC cells may also be propagated under specific conditions to become "pluripotent." The term "pluripotent stem cells" describes stem cells that are capable of differentiating into any type of body cell, when cultured under conditions that give rise to the particular cell type.

The MAFSCs are preferably isolated from humans. However, the MAFSCs may be isolated in a similar manner from other species. Examples of species that may be used to derive the MAFSCs include but are not limited to mammals, humans, primates, dogs, cats, goats, elephants, endangered species, cattle, horses, pigs, mice, rabbits, and the like.

The amniotic fluid-derived cells and MAFSC can be recognized by their specific cell surface proteins or by the presence of specific cellular proteins. Typically, specific cell types have specific cell surface proteins. These surface proteins can be used as "markers" to determine or confirm specific cell types. Typically, these surface markers can be visualized using antibody-based technology or other detection methods. One method of characterizing cellular markers, FACS analysis, is described in Example 3.

The surface markers of the isolated MAFSC cells derived from independently-harvested amniotic fluid samples were tested for a range of cell surface and other markers, using monoclonal antibodies and FACS analysis (see Example 3 and Table 1). These cells can be characterized by the following cell surface markers: SSEA3, SSEA4, Tra-1-60, Tra-1-81, Tra-2-54, as shown in FIG. 3. The MAFSC cells can be distinguished from mouse ES cells in that the MAFSC cells do not express the cell surface marker SSEA1. Additionally, MAFSC express the stem cell transcription factor Oct-4. The MAFSC cells can be recognized by the presence of at least one, or at least two, or at least three, or at least four, or at least five, or at least six, or all of the following cellular markers SSEA3, SSEA4, Tra-1-60, Tra-1-81, Tra-2-54 and Oct-4.

In some embodiments of the present invention, the SSEA3 marker is expressed in a range of from about 90%, 92%, 94% to about 96%, 98%, 99%, or 100% of the cells in the MAFSC culture. The SSEA4 marker can be expressed, for example, in a range of from about 90%, 92%, 94% to about 96%, 98%, 99%, or 100% of the cells in the MAFSC culture. In some embodiments of the present invention, the Tra-1-60 marker expressed, for example, in a range of from about 60%, 65%, or 70% to about 85%, 90%, or 95% of the cells in the MAFSC culture. In some embodiments of the present invention, the Tra-1-81 marker is expressed in a range of from about 70%, 75%, or 80% to about 85%, 90%, or 95% of the cells in the MAFSC culture. The Tra-2-84 marker can be expressed, for example, in a range of from about 55%, 60%, 65%, or 70% to about 80%, 90%, or 95% of the cells in the MAFSC culture. In some embodiments of the present invention, the Oct-4 marker is expressed in a range of from about 25%, 30%, 35%, or 40% to about 45%, 55%, 65%, or 70% of the cells in the MAFSC culture.

The MAFSC cultures express very little or no SSEA-1 marker. For example, Table 1 shows that 3.3% of the MAFSC cells express the SSEA-1 marker. This very low level of expression is considered to be at (or very near to) background level.

The C-kit gene encodes a tyrosine kinase growth factor receptor for stem cell factor (SCF). In some embodiments of the invention, the MAFSC cells are not C-kit positive. In additional embodiments, the MAFSC cells may produce very low levels of C-kit.

In addition to the embryo stem cell markers shown in FIG. 3, and Table 1, MAFSC cells also expressed high levels of the cell surface antigens that are normally found on human mesenchymal stem cells, but not normally on human embryo stem cells (M F Pittinger et al., Science 284:143-147, 1999; S Gronthos et al., J. Cell Physiol. 189:54-63, 2001). This set of markers includes CD13 (99.6%) aminopeptidase N, CD44 (99.7%) hyaluronic acid-binding receptor, CD49b (99.8%) collagen/laminin-binding integrin alpha2, and CD105 (97%) endoglin. The presence of both the embryonic stem cell markers and the hMSC markers on the MAFSC cell cultures indicates that amniotic fluid-derived MAFSC cells, grown and propagated as described here, represent a novel class of human stem cells that combined the characteristics of hES cells and of hMSC cells.

In some embodiments of the invention, at least about 90%, 94%, 97%, 99%, or 100% of the cells in the MAFSC culture express CD13. In additional embodiments, at least about 90%, 94%, 97%, 99%, or 100% of the cells in the MAFSC culture express CD44. In some embodiments of the invention, a range from at least about 90%, 94%, 97%, 99%, 99.5%, or 100% of the cells in the MAFSC culture express CD49b. In further embodiments of the invention, a range from at least about 90%, 94%, 97%, 99%, 99.5%, or 100% of the cells in the MAFSC culture express CD105.

In a particularly advantageous embodiment, the MAFSC cells are human stem cells that can be propagated for an indefinite period of time in continuous culture in an undifferentiated state. The term "undifferentiated" refers to cells that have not become specialized cell types. Typically, the cells are grown in a nutrient medium such as the medium shown in Example 1. A "nutrient medium" is a medium for culturing cells containing nutrients that promote proliferation. The nutrient medium may contain any of the following in an appropriate combination: isotonic saline, buffer, amino acids, antibiotics, serum or serum replacement, and exogenously added factors.

The MAFSC cells may also be "banked" or stored in a manner that allows the cells to be revived as needed in the future, as disclosed in co-pending Patent Application Ser. No. 60/495,513, which is incorporated by reference herein in its entirety. An aliquot of the undifferentiated cells can be removed at any time, to be differentiated into a particular cell type or tissue type, and may then be used to treat a disease or to replace malfunctioning tissues in a patient. Since the cells are harvested from the amniotic fluid, the cells can be stored so that an individual can have access to his or her own undifferentiated cells for an entire lifetime.

The MAFSCs may be grown in an undifferentiated state for as long as desired (and optionally stored as described above), and can then be cultured under certain conditions to allow progression to a differentiated state. By "differentiation" is meant the process whereby an unspecialized cell acquires the features of a specialized cell such as a heart, liver, muscle, pancreas or other organ or tissue cell. The MAFSCs, when cultured under certain conditions, have the ability to differentiate in a regulated manner into three or more subphenotypes. Once sufficient cellular mass is achieved, cells can be differentiated into endodermal, mesodermal and ectodermal derived tissues in vitro and in vivo. This planned, specialized differentiation from undifferentiated cells towards a specific cell type or tissue type is termed "directed differentiation." Exemplary cell types that may be prepared from MAFSCs using directed differentiation include but are not limited to fat cells, cardiac muscle cells, epithelial cells, liver cells, brain cells, blood cells, neurons, glial cells, pancreatic cells, and the like.

General methods relating to stem cell differentiation techniques that may be useful for differentiating the MAFSCs of this invention can be found in general texts such as: Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998); and in Stem cell biology (L. M. Reid, Curr. Opinion Cell Biol. 2:121, 1990), each of which is incorporated by reference herein in its entirety.

Differentiation agents, maturation agents, or maturation factors may be useful to allow progression to certain cell types. Examples of differentiation agents, that may be used include but are not limited to agents, such as N-butyrate, which are useful for differentiating embryonic stem cells to liver cells are described in U.S. Pat. No. 6,506,574, to Rambhatla et al. Optionally, maturation agents, or maturation factors, such as, for example, growth factors, peptide hormones, cytokines, ligand receptor complexes, corticosteroids, retinoic acid, and even organic solvents like DMSO have been found to effect differentiation of embryonic stem cells (U.S. Pat. No. 6,506,574). Other suitable differentiating or maturation agents which may be used include but are not limited to a glucocorticoid with cAMP-elevating agents, methyl-isobutylxanthine, indomethacin, and the like.

In additional embodiments, the amniotic fluid-derived MAFSC cells described herein may additionally be used to prepare "feeder cells" for embryonic stem cell preparations. Different MAFSC cultured strains, such as short-term cultured MAFSC cultures, or long term MAFSC cultures (for example, "MAFSC #111a") may be especially useful for providing feeder layers. "Feeder cells" are terms used to describe cells of one type that are co-cultured with cells of a second type, to provide an environment in which the cells of the second type can be maintained, or proliferate. Feeder cells used to grow and maintain human embryonic stem cells need not be immortal and different MAFSC cultures, irrespective of their mortality state may support hES cell establishment and/or propagation.

The isolated MAFSCs or their derivatives may be used to treat diseases in humans or animals. As used herein the term "treat" or "treatment" refer to both therapeutic treatment and prophylactic or preventative measures, wherein the object is to prevent, slow down (lessen), or reverse an undesired physiological change or disorder. The term "treat" also refers to the characterization of the type or severity of disease which may have ramifications for future prognosis, or need for specific treatments. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

To treat a human or animal in need of treatment, the MAFSCs can be either regenerated into segments of a desired tissue, then transplanted into the patient, or can be regenerated into a whole tissue that will be used to replace the failing tissue, or can be injected into a tissue of interest as whole cells, where they will regenerate at the injected location.

It may be possible to replace any type of failing tissue with MAFSC-derived cells. MAFSCs may be differentiated into tissues such as liver, endocrine tissues, lung, blood cells, neuronal or astroglial cells, or others, which may then be used for transplantation to cure or treat diseases. Examples of diseases that may be treated with MAFSC-derived cells or tissues include but are not limited to cirrhosis of the liver, pancreatitis, diabetes, Parkinson's disease, spinal cord injury, stroke, burns, heart disease, certain types of cancer, osteoarthritis, rheumatoid arthritis, leukemia, lymphoma, genetic blood disorders, and brain disorders such as Alzheimer's disease.

Additional examples of diseases that can be treated with amniotic fluid-derived cell-derived stem cells include but are not limited to Acute Lymphoblastic Leukemia, Acute Myelogenous Leukemia, Acute Biphenotypic Leukemia, and Acute Undifferentiated Leukemia; Chronic Myelogenous Leukemia, Chronic Lymphocytic Leukemia, Juvenile Chronic Myelogenous Leukemia, Juvenile Myelomonocytic Leukemia, Refractory Anemia, Refractory Anemia with Ringed Sideroblasts, Refractory Anemia with Excess Blasts, Refractory Anemia with Excess Blasts in Transformation, Chronic Myelomonocytic Leukemia, Aplastic Anemia, Fanconi Anemia, Paroxysmal Nocturnal Hemoglobinuria, Pure Red Cell Aplasia, Acute Myelofibrosis, Agnogenic Myeloid Metaplasia, myelofibrosis, Polycythemia Vera, Essential Thrombocythemia, Non-Hodgkin's Lymphoma, Hodgkin's Disease, Chediak-Higashi Syndrome, Chronic Granulomatous Disease, Neutrophil Actin Deficiency, Reticular Dysgenesis, Mucopolysaccharidoses, Hurler's Syndrome, Scheie Syndrome, Hunter's Syndrome, Sanfilippo Syndrome, Morquio Syndrome, Maroteaux-Lamy Syndrome, Sly Syndrome, Beta-Glucuronidase Deficiency, Adrenoleukodystrophy, Mucolipidosis II, Krabbe Disease, Gaucher's Disease, Niemann-Pick Disease, Wolman Disease, Metachromatic Leukodystrophy, Familial Erythrophagocytic Lymphohistiocytosis, Histiocytosis-X, Hemophagocytosis, Inherited Erythrocyte Abnormalities, Beta Thalassemia Major, Sickle Cell Disease, Inherited Immune System Disorders, Ataxia-Telangiectasia, Kostmann Syndrome, Leukocyte Adhesion Deficiency, DiGeorge Syndrome, Bare Lymphocyte Syndrome, Omenn's Syndrome, Severe Combined Immunodeficiency, Common Variable Immunodeficiency, Wiskott-Aldrich Syndrome, X-Linked Lymphoproliferative Disorder, Other Inherited Disorders, Lesch-Nyhan Syndrome, Cartilage-Hair Hypoplasia, Glanzmann Thrombasthenia, Osteopetrosis, Inherited Platelet Abnormalities, Amegakaryocytosis, Congenital Thrombocytopenia, Plasma Cell Disorders, Multiple Myeloma, Plasma Cell Leukemia, Waldenstrom's Macroglobulinemia, Breast Cancer, Ewing Sarcoma, Neuroblastoma, Renal Cell Carcinoma, brain disorders such as Alzheimer's disease, and the like (see, for example, hypertext transfer protocol (http) on the world wide web at: marrow.org/index.html, which is incorporated by reference herein in its entirety).

Many different types of tissues may be replaced, in full or in part, using the differentiated cells derived from the MAFSC cells, as described herein. Examples of tissues which may be (at least partially) replaced include, but are not limited to, lung tissue, heart tissue, ocular tissue, nerve tissue, brain tissue, muscle tissue, skin, pancreatic beta cells, and the like.

MAFSCs or MAFSC-derived cells may also be genetically modified by transfection with any suitable gene of interest. General techniques useful to genetically modify the MAFSC cells (or their derivatives) can be found, for example, in standard textbooks and reviews in cell biology, tissue culture, and embryology. Methods in molecular genetics and genetic engineering are described, for example, in Molecular Cloning: A Laboratory Manual, 2nd Ed. (Sambrook et al., 1989); Oligonucleotide Synthesis (M. J. Gait, ed., 1984); Animal Cell Culture (R. I. Freshney, ed., 1987); the series Methods in Enzymology (Academic Press, Inc.); Gene Transfer Vectors for Mammalian Cells (I. M. Miller & M. P. Calos, eds., 1987); Current Protocols in Molecular Biology and Short Protocols in Molecular Biology, 3rd Edition (F. M. Ausubel et al., eds., 1987 & 1995); and Recombinant DNA Methodology II (R. Wu ed., Academic Press 1995); each of which is incorporated by reference herein in its entirety.

The nucleic acid molecule of interest can be stably integrated into the genome of the host MAFSC cell, or the nucleic acid molecule and can also be present as an extrachromosomal molecule, such as a vector or plasmid. Such an extrachromosomal molecule can be auto-replicating. The term "transfection," as used herein, refers to a process for introducing heterologous nucleic acid into the host MAFSC or MAFSC-derived cell or tissue. A transfected MAFSC cell refers to a MAFSC cell into which a heterologous nucleic acid molecule has been introduced. One example of a useful genetic modification of a MAFSC cell is the insertion of the "TERT" gene (telomerase reverse transcriptase), as described in Example 6. MAFSC Cells that have been transduced with vectors expressing the TERT sequence have become immortal and could be expanded for an unlimited period of time. Further, genetic modification of MAFSC cells can be used for gene therapy purposes, such as the administration of a gene encoding a functional protein product to an individual that lacks a functional copy of a gene of interest. If desired, MAFSC cells or their derivatives can also be genetically modified to inhibit the expression of certain genes, using gene manipulation methods known in the art.

It will be understood by those of skill in the art that numerous and various modifications can be made without departing from the spirit of the present invention. A more complete understanding can be obtained by reference to the following specific examples which are provided herein for purposes of illustration only and are not intended to limit the scope of the invention.

EXAMPLES

Example 1

Isolation and Expansion of Undifferentiated Cells Derived from Amniotic Fluid

Approximately 2 to 5 ml of fresh amniotic fluid was harvested from women undergoing routine amniocentesis at 16 to 21 weeks of pregnancy ($2^{nd}$ trimester). Second trimester amniotic fluid contained approximately $1$-$2 \times 10^4$ live cells per ml. The cells were pelleted in a clinical centrifuge and resuspended in 15 ml "MAFSC" medium. MAFSC medium was composed of low glucose Dulbecco Modified Eagle's Medium (GIBCO, Carlsbad, Calif.) and MCDB 201 medium (SIGMA, Saint Louis, Mo.) at a one to one ratio and contained 2% Defined Fetal Calf Serum (HYCLONE, Logan, Utah), 1× insulin-transferrin-selenium, linoleic-acid-bovine-serum-albumin (ITS+1, SIGMA), 1 nanomolar dexamethasone (Sigma), 100 µm ascorbic acid 2-phosphate (Sigma), 4 µm/ml gentamycin, 10 ng/ml of rhEGF (R&D Systems, Minneapolis, Minn.), 10 ng/ml rrPDGF-BB (R&D) and 10 ng/ml rhFGF-basic (R&D). The wells of 6-well culture dishes were prepared for cell plating by coating for one hour at room temperature with 2.5 ml of fibronectin (stock of 10 µg fibronectin/ml of sterile water) immediately prior to cell plating. The fibronectin solution was removed prior to cell plating and the wells were not washed after removal of the fibronectin solution. The cells were then seeded in 2.5 ml of medium in each well.

The cells in MAFSC culture appeared under the inverted phase microscope as large suspension cells that divided on average once every 4 days, but ceased dividing 8-12 days after seeding. The growth medium of MAFSC cultures was changed with complete MAFSC medium every two days making sure to not lose the suspended cells. After 8-10 days, small numbers of adherent cells emerged which grew into large colonies of >$10^5$ cells in 14-15 days. On average, 0-1 adherent colonies grew out per $2 \times 10^4$ live cells seeded. Hence, a sample of 5 ml of fresh amniotic fluid gave rise to 3-5 adherent cell colonies, resulting in a single colony/clone in the majority of the wells of 6-well cell culture clusters.

Cells were transferred to successively larger fibronectin-coated flasks/vessels. To perform cell transfer, the cells were grown to a subconfluent state of approximately 40% confluence and were detached with 0.25% Trypsin-EDTA and replated at a 1:3 or 1:12 dilution under the same culture conditions.

Example 2

Morphological Characterization of Cell Types

Cultured amniotic fluid-derived cells were tested for cell surface and differentiation markers and were karyotyped. These cells were found to be immortal or near-immortal and were named Multipotent Amniotic Fetal Stem Cells (MAFSC).

Figure 1B:
Figure 1C:
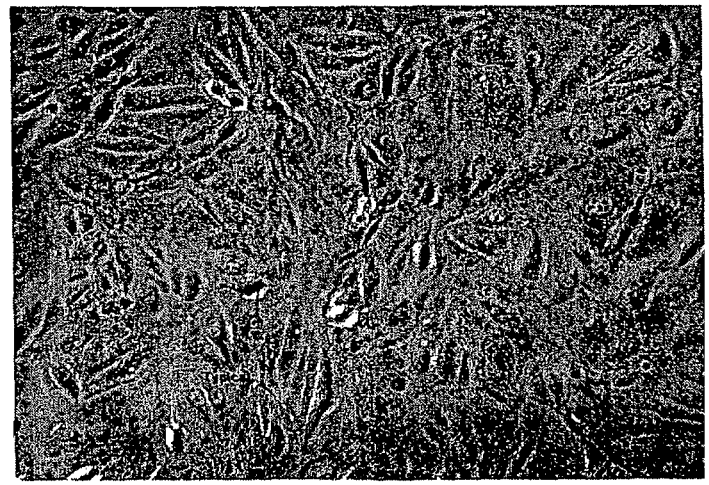

All of >80 amniotic fluid sample harvests of 5 ml gave rise to at least one adherent MAFSC colony and continuous culture. The majority of sample harvests gave rise to 3-4 individual clones. Among the individual clones, different colonies/cultures had diverse colony morphologies, as shown in FIG. 1. Some cultures had a flat, epihelial morphology (FIG. 1A). Others had a fibroblastic morphology (FIGS. 1B, 1C). Both the epithelioid and the fibroblastic classes of cultures senesced after ~60 population doublings (PD), yielding a maximum of $10^{18}$ cells, unless the cells were immortalized by the expression of the human TERT (telomerase) gene that maintained the length of the cells' telomeres. Indeed, mortal MAFSC cultures have been immortalized at low (PD 15-25) transfer numbers by infection with an amphotropic high titer retroviral vector expressing the human TERT gene. MAFSC cultures immortalized with TERT have not senesced after >220 population doublings. Thus, the TERT-modified MAFSC cultures were immortal, though only after genetic modification which may not be the advantaged way to derive human stem cell strains.

Figure 2A:
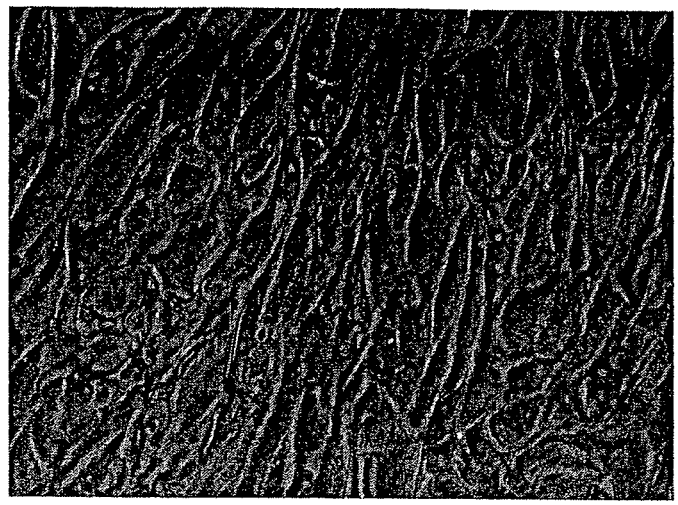
FIGS. 2A and 2B are photographs showing the morphology of MAFSC cell clones/cultures that behave like immortal cell lines.
Figure 2B:
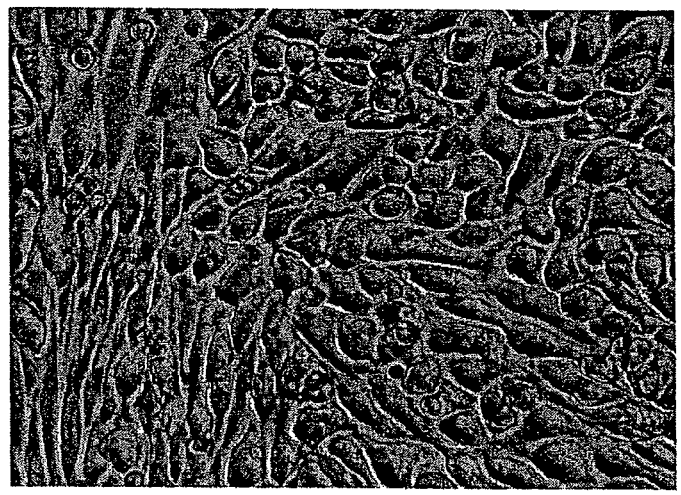

About half of the amniotic fluid samples gave rise to MAFSC clones/cultures that behaved like immortal cell lines, as shown in FIGS. 2A and 2B. These cultures grew vigorously, with a doubling time of 28 hours. When confluent, the cells piled up in multilayered fashion and numerous round, semi-detached cells grew on top of a swirling, non-contact-inhibited layer of cells. These aggressive cultures expressed the telomerase gene/protein. The cells were cloneable into single cell clones and are non-senescing. These vigorously growing MAFSC lines expressed very high levels of a set of cell surface determinants known to be present on non-differentiated human Embryo Stem Cells (hES) and expressed a set of surface determinants known to be associated with non-differentiated human Mesenchymal Stem Cells (MSC). MAFSC cells did not express markers characteristic of hematopoietic cells, e.g. CD45 and CD34, see FIGS. 3 and 4, which show flow cytometry examples of one such vigorous MAFSC line, #111a.

Example 3

FACS Analysis of MAFSC Cells

Cells were prepared for FACS analysis by trypsinizing to remove them from the tissue culture flask, washing in buffer, HBSS, 2% BSA, 0.1% sodium azide, then resuspended in 100 µL of the same buffer. For intracellular antigens (i.e. Oct-4), the cells were fixed and permeablized using Beckman-Coulter IntraPrep reagents, as suggested by the manufacturer. Primary antibodies specific for the indicated cell-surface or intracellular marker were added at a 1:10 dilution and incubated for 30 minutes at room temperature, then washed. For samples using primary antibodies that were not fluorescently-conjugated, the cells were then resuspended in 250 µL of buffer and the appropriate fluorescent-labeled secondary antibody was added at a 1:250 dilution and incubated for 30 minutes at room temperature. Labeled cells were washed and resuspended in buffer or 1% paraformaldehyde for analysis by a FACSCalibur flow cytometer. The data obtained from this analysis were plotted as the x-axis being the number of cells analyzed per point and the y-axis indicating the logarithm of fluorescent intensity of the antibody-labeled cells. The fluorescence was compared to control cells that were not labeled with antibody, to discount any background fluorescence. The percent indicated was the fraction of cells that were positive for the specific antibody-labeled antigen. The level of antibody label (X-axis) is proportional to the concentration of the specific antigen present on the cells.

Example 4

Stem Cell Markers on MAFSC Cells

MAFSC lines expressed very high levels of a set of cell surface determinants known to be present on non-differentiated human Embryo Stem Cells (hES) and expressed a set of surface determinants known to be associated with non-differentiated human Mesenchymal Stem Cells (MSC). MAFSC cells did not express markers characteristic of hematopoietic cells, e.g. CD45 and CD34, see FIGS. 3 and 4, which show flow cytometry examples of one such vigorous MAFSC line, #111a. The flow cytometry was performed as described above in Example 3.

Mass cultures of the MAFSC cells strain 111a were characterized by very high expression of the globoseries glycolipid antigens SSEA3 (96%), SSEA4 (96%), the lack of expression of a lactoseries oligosaccharide antigen, SSEA1, the expression of the keratin sulphate-related antigens Tra-1-60 (71%) and Tra-1-81 (82%) and the tissue non-specific alkaline phosphatase-related antigen Tra-2-54 (63%), FIG. 3. The expression (or lack of expression, SSEA1) of these antigens is expressly exhibited by pluropotential, undifferentiated human embryo stem cells in which the expression of these antigens is lost (or gained, SSEA1) by the induction of differentiation with retinoic acid (Draper J S, Pigott C, Thompson J A, Andrews P W. 2002 Journal of Anatomy 200: 249-258). MAFSC cells expressed high levels of HLA Class I but not of HLA Class II, low levels of CD117 (c-kit ligand) and Stro-1, FIG. 3.

In addition to the embryo stem cell markers shown in FIG. 3 and discussed in Table 1, MAFSC cells (such as, for example the MAFSC 111a line), expressed high levels of the antigen CD13 (99.6%) aminopeptidase N, CD44 (99.7%) hyaluronic acid-binding receptor, CD49b (99.8%) collagen/laminin-binding integrin alpha2, and CD105 (97%) endoglin. This set of cell surface antigens is found on human mesenchymal stem cells but not normally on human embryo stem cells (M F Pittinger et al., Science 284:143-147, 1999; S Gronthos et al., J. Cell Physiol. 189:54-63, 2001). Hence, the amniotic fluid-derived MAFSC cells, grown and propagated as described here, represent a novel class of human stem cells that combined the characteristics of hES cells and of hMSC cells and can be expected to differentiate into many diverse directions.

The amniotic fluid-derived stem cells also expressed the transcription factor OCT-4. The human embryonic stem cell markers typically found on MAFSC cells are shown in Table 1 and are data obtained for MAFSC cells, clone 111a, cultured for >40 population doublings in MAFSC culture medium. The markers typically displayed by long term MAFSC cells are compared with the same markers found on fresh amniotic fluid-derived cells, "AES", and with various control cells, the human embryonic carcinoma cell line NTERA-4; amniotic-fluid-derived, long-term fibroblasts, MY-TERT, immortalized by the human telomerase reverse transcriptase gene, TERT; and normal human foreskin fibroblasts, HFF.

example of a useful genetic modification of a MAFSC cell is the insertion of the "TERT" gene (human telomerase reverse transcriptase, GenBank Accession No. NM_003219). A retroviral MSCV vector of titer $3\times10^6$ infectious units/ml was prepared and introduced into MAFSC cells by infection as amphotropic virus. The vector contained a selectable marker gene and the gene encoding "TERT", operably linked to the MSCV promoter sequence. The vector was used to stably transduce MAFSC cells. Stably transduced cells were then selected using the G418-selection agent corresponding to the selectable marker gene. Expression of TERT was then confirmed using antibody-based detection procedures. Mortal MAFSC strains that were transduced with the MSCV-TERT vector could be significantly expanded and were essentially immortal.

Examples 7-10

As mentioned previously, the MAFSC cells can be differentiated to may cell types. For example, MAFSC cells differentiated into cells of Ectoderm, Mesoderm and Endoderm. In addition to the differentiation paths exemplified below, MAFSC cells are capable of other, pluripotent differentiation paths.

TABLE 1

| | Embryonic Stem Cell Markers | | | | |
|---|---|---|---|---|---|
| Marker (% Positive) | MAFSC 111a Cultured Amniocytes | "AES" Fresh Amniocytes | NTERA-4 Embryonic Carcinoma Line | MY-Tert Immortal Amnio-fibroblasts | HFF Foreskin Fibroblasts |
| SSEA-1 | 3.3 | n.d.* | 3.8 | 2 | 1.5 |
| SSEA-3 | 96 | 19.4 | 9.1 | 17.3 | 2.3 |
| SSEA-4 | 96 | 39.8 | 96.8 | 67.8 | 8.2 |
| Tra-1-60 | 71 | 48.9 | 99.8 | 4.9 | 1.7 |
| Tra-1-81 | 82 | 42 | 99.6 | 2.8 | 1.7 |
| Tra-2-54 | 63 | 30.4 | 99.2 | 16.1 | 27.9 |
| Oct-4 | 39 | 12.7 | 99 | 2.6 | 3.4 |

*n.d. = not determined

Example 5

MAFSC Cells do not Have Tumorigenic Properties

Unlike fetal stem cells, MAFSCs do not have tumorigenic properties. To assess this, approximately $10^6$ fresh amniotic fluid derived stem cells were injected intramuscularly into SCID/Beige mice. The mice were tested for tumorigenicity at three months after injection. No tumors were found. In contrast, human teratoma cells NTERA that were injected similarly in the muscle of separate mice, gave rise to frank teratomas in 5 weeks.

Example 6

Genetic Modification of MAFSCs to Express the TERT Gene to Alter MAFSC Properties As mentioned above, MAFSCs or MAFSC-derived cells may also be genetically modified by transfection with any suitable gene of interest. The nucleic acid molecule can be stably integrated into the genome of the host MAFSC cell, or the nucleic acid molecule and can also be present as an extrachromosomal molecule, such as a vector or plasmid. One Examples 7 through 10 below describe methods of differentiating MAFSC cells into adipogenic cells, chondrogenic cells, osteogenic cells, and neural cells. Additional differentiation methods are known in the art and can be found, for example, in U.S. Pat. No. 5,827,740; Yoo J U, et al., Jour. Bone Joint Surg. (1998) 80-A(12):1745-1757; Jaiswal N, et al., Journal of Cellular Biochem (1997) 64:295-312; Tsai M-S, et al., Human Reproduction (2004) 19(6):1450-1456; Kögler G, et al; J. Experimental Med (2004) 200(2):123-135; and Lodie T A et al, Tissue Eng (2002) 8(5):739-753; each of which is incorporated by reference herein in its entirety.

Example 7

Method of Adipogenic Differentiation of MAFSC Cells

Figure 2C:
FIG. 2C shows a culture of MAFSC strain 111a cells which have been differentiated into adipocytes using the method described in Example 7.
Figures 3A, 3B, 3C, 3D, 3E:
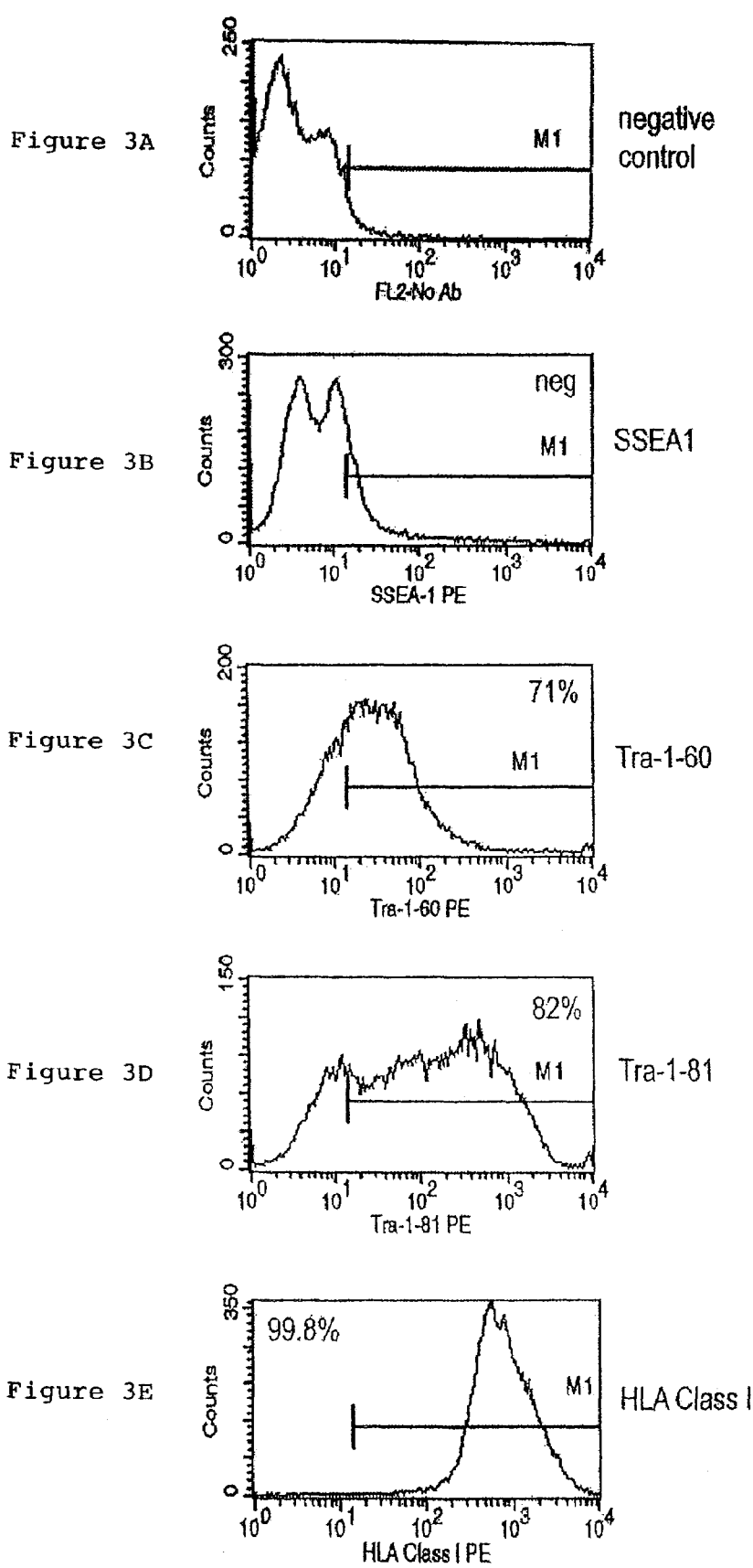
FIGS. 3A and 3J are the negative controls.
Figure 3F:
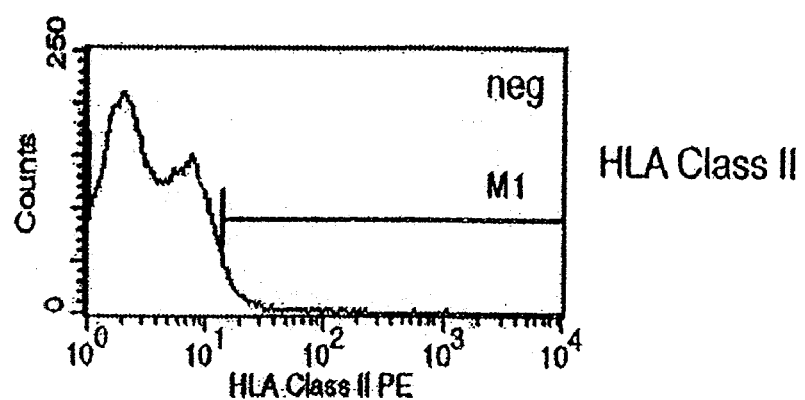
FIG. 3 shows FACS analysis of the % of cells expressing various human ES cell-associated antigens by MAFSC cells. The markers shown are SSEA1 (FIG. 3B), Tra-1-60 (FIG. 3C), Tra-1-81 (FIG. 3D), HLA Class1 (FIG. 3E), HLA Class II (FIG. 3F), CD34 (FIG. 3G), CD117 (FIG. 3H), Stro-1 (FIG. 3I), SSEA3 (FIG. 3K), SSEA4 (FIG. 3L), Tra-2-54 (FIG. 3M), and CD45 (FIG. 3N).
Figure 3G:
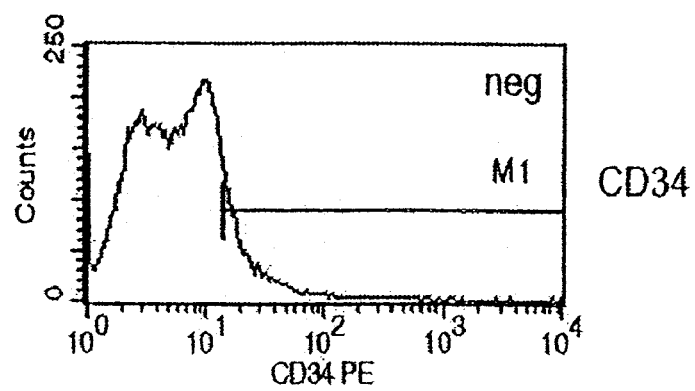
Figure 3H:
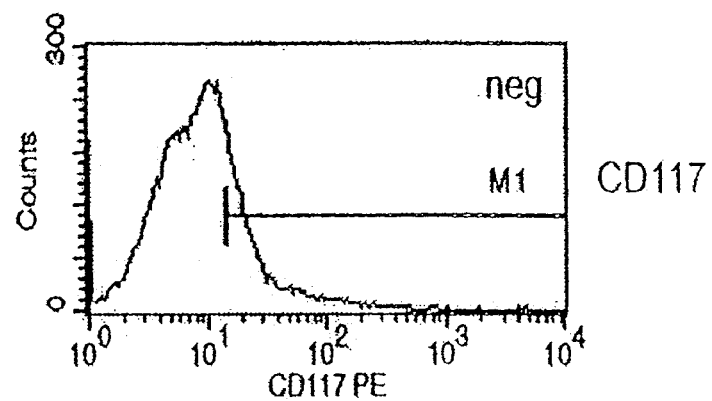
Figure 3I:
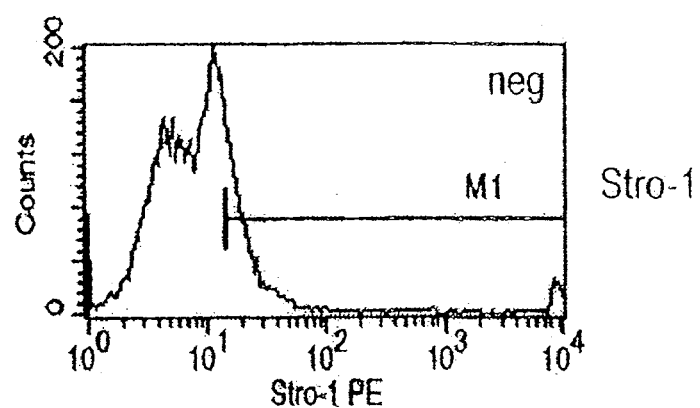
Figure 3J:
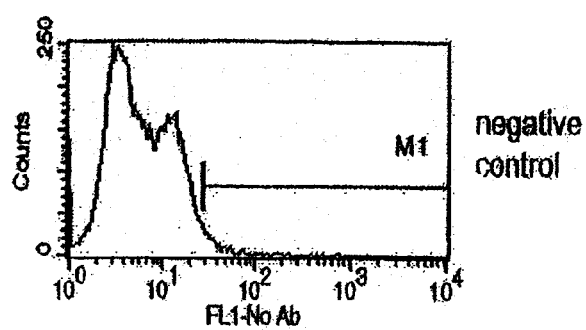
Figure 3K:
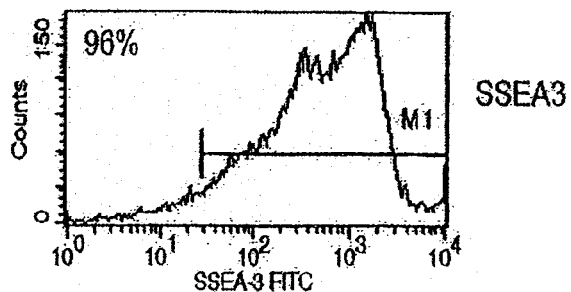
Figure 3L:
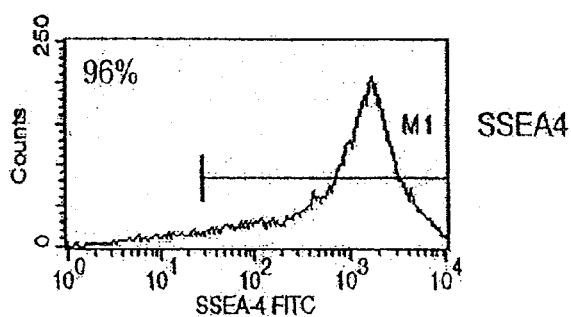
Figure 3M:
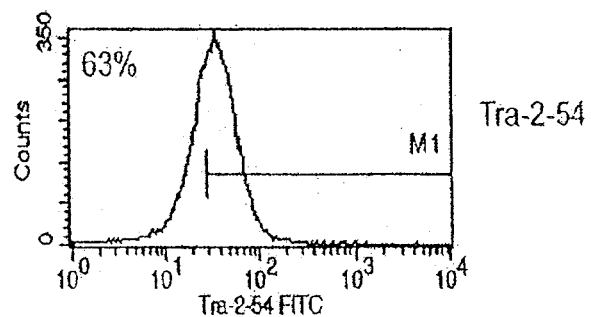
Figure 3N:
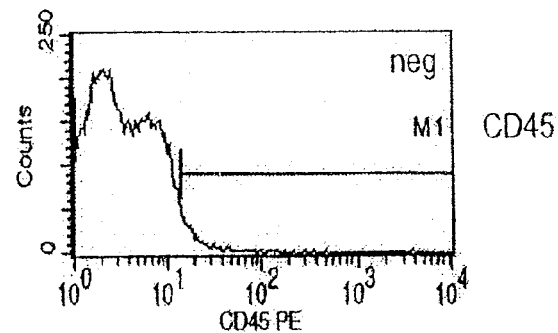
Figure 4A:
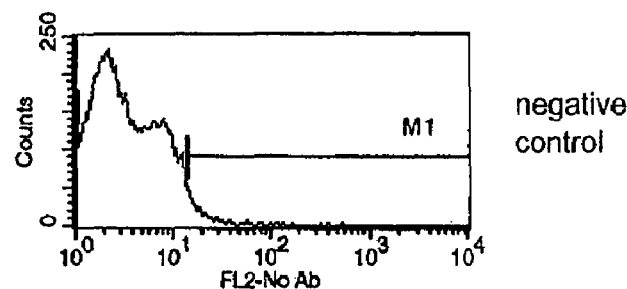
FIG. 4A is the negative control.
Figure 4B:
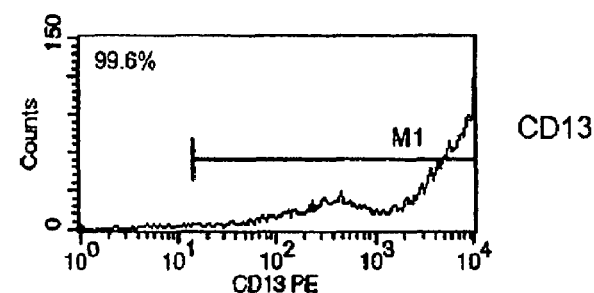
FIG. 4 illustrates the expression of human MSC-associated antigens by MAFSC cells, as shown by FACS analysis of the % of cells in the culture that are positive for the marker. The markers shown are CD13 (FIG. 4B), CD44 (FIG. 4C), CD49b (FIG. 4D), and CD105 (FIG. 4E).
Figure 4C:
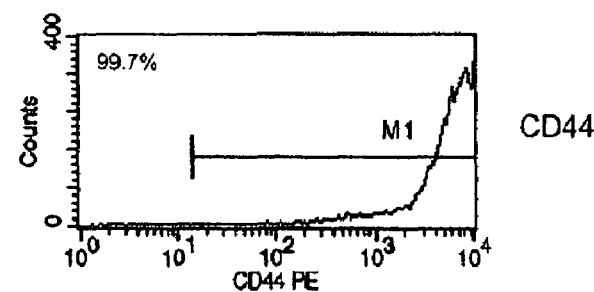
Figure 4D:
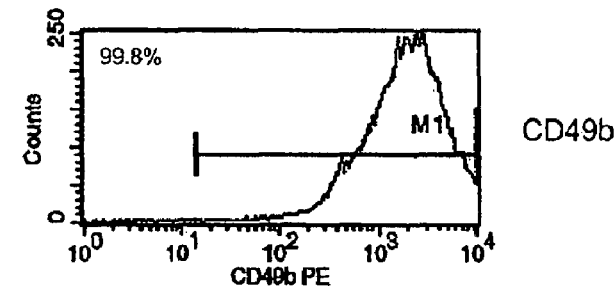
Figure 4E:
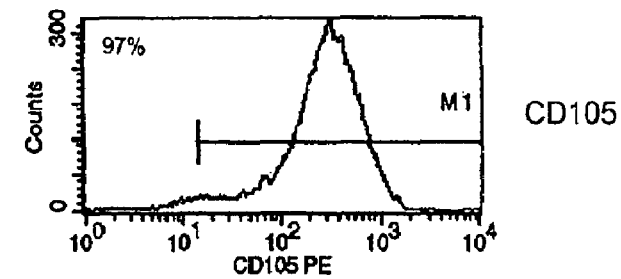

The method described below was used to differentiate MAFSC cells into adipogenic cells. FIG. 2C shows a culture of MAFSC strain 111a cells differentiated into adipocytes, as indicated by the inclusion of small and large fat deposits that stained positive with Oil Red O (not shown).

Media: —normal hMSC media: DMEM (low glucose), 10% FBS and gentamycin.

Adipogenic induction Media: DMEM (low) with 10% FBS containing 10 μg/ml insulin, 0.5 mM methyl-isobutylxanthine (IBMX), 1 μM dexamethasone, 100 μM indomethacin.

Adipogenic Maintenance media: DMEM containing 10% FBS and 10 μg/ml insulin.

Note: dexamethasone is a gluticorticoid which is typically used at a concentration of between about 0.5 μM and about 2.0 μM. Both IBMX and indomethacin are inhibitors of cAMP degradation and are typically used at a concentration range of between about 0.2 and about 2 mM.

Differentiation Protocol: The cells were grown until colonies were well established, then subcultured into 35-mm tissue culture dishes at $10^5$ cells per dish. The cells were fed with 2 ml normal hMSC media and maintained at 37° C., 5% $CO_2$ and 90% humidity. The fluid was changed every three days, and the culture was allowed to become confluent. The cells were then cultured for an additional 3-7 days. The post confluence culturing procedure enhanced adipogenic response at least out to about 14 days. The medium was then replaced with 2 ml Adipogenic Induction media and incubated for 48 hours. The medium was next replaced with Adipogenic Maintenance Media, changing cells every 3-4 days. Using this method, lipid vacuoles became visible in about 3-7 days and became more numerous and larger over time, for up to about 30 days. The cells were then prepared for Oil Red O histology staining by rinsing with PBS, pelleting and putting in an OCP block (avoiding Etoh), and freezing with dry ice.

Verification Protocol: The adipogenic cells were verified using several methods. Verification by direct microscopy involved the examination of cells for lipid vacuoles within cells. The cells were stained with lipid soluble dyes (Nile Red and Oil Red O) and were examined under epifluorescence illumination. Verification by measuring adipose associated gene products by immunoblotting was performed using an antibody to aP2, or cDNA probes for LPL and PPAR?2. Additionally, histochemical detection methods, such as to a-smooth muscle actin, CD44, and CD146, were also performed.

Example 8

Method of Chondrogenic Differentiation of MAFSCs

The method described below was used to differentiate the MAFSC cells into Chondrogenic cells.

Ingredients:
Normal hMSC medium: DMEM low glucose, 100 U/ml penicillin, 100 μg/ml gentamycin, 250 ng/ml amphotericin B, and 10% FBS Incomplete chondrogenic medium: high glucose DMEM, 100 nM dexamethasone, 50 μg/ml ascorbic acid 2 phosphate, 100 μg/ml sodium pyruvate, and ITS+1 (ITS+1=final concentration of 6.25 μg/ml bovine insulin, 6.25 μg/ml transferrin, 6.25 μg/ml selenous acid, 5.33 μg/ml linoleic acid, and 1.25 mg/ml bovine serum albumin).

Complete Chondrogenic medium: Incomplete medium supplemented with 10 ng/ml TGF-β3.

TGF-β3 stock: 2 μg/200 μl (=10 ng/μl) in 4 mM HCL supplemented with 1 mg/ml BSA or HSA.

Note: store stock solution in small aliquots in freezer-safe tubes and store $\leq 70°$ C. for no more than 6 mo. Working stock kept at 4° C.

Add 1 ul of TGF-β3 to 1 ml of incomplete medium to make complete medium; must be prepared fresh every time and used within 12 hours.

Differentiation Protocol: Cells were grown in normal hMSC medium in tissue culture flasks in a 5% $CO_2$ atmosphere at 37° C. Cells were passaged twice a week and use at passage 1, 2, or 3. After 10-14 days when colonies were evident, cells were trypsinized (0.25% trypsin and 0.05 mM EDTA in D-PBS), washed in serum-containing medium and resuspended in chondrogenic complete medium to $2.5 \times 10^5$ cells per 0.5 ml chondrogenic complete medium. Cells were then transferred to 15 ml conical polypropylene centrifuge tubes. Cells were centrifuged for 5 min at 600 g, leaving both medium and cell pellet in tubes. Tubes were placed in an incubator with caps loosened to permit gas exchange. Sedimented cells formed a spherical mass at bottom of tube w/in 24 hours. The fluid was replaced with chondrogenic complete medium three times per eek for up to 21 days. The cells were prepared for staining by fixing the pellet with 10% formalin.

Verification protocol: the chondrogenic cells were verified by the presence of a multi-layered matrix rich morphology, and increased proteoglycan-rich extracellular matrix during culture by histology using Safranin O stain. Other verification methods included the detection of IHC-type II collagen using a monoclonal antibody C4F6, as well as RT-PCR for Collagen Type II and IX and osteopontin. Cell fixation was performed by rinsing cell pellets in D-PBS, fixing for 1 h in 4% formaldehyde in D-PBS, transferring samples into 70% ethanol, dehydrating in ethanol and xylene series, then embedding in paraffin. 5 μm sections were cut through the center of each pellet. Sections were treated with 0.3% $H_2O_2$ in methanol (30 min) to abolish endogenous peroxidase. The sections were digested for 30 min with 50 uU/ml chondroitinase ABC in 100 mM Tris-acetate, pH 7.6, and 0.1% bovine serum albumin.

Example 9

Method of Osteogenic Differentiation of MAFSC Cells

To differentiate MAFSC cells to osteogenic cells, the following method is used.

Media:
Control medium: DMEM (low glucose) with 10% FBS.
Osteogenic medium: DMEM with 10% FBS+100 nM Dexamethasone, 10 mM B-glycerol phosphate, 0.05 mM AsAP (Ascorbate).

Differentiation protocol: Cells are grown in control medium at 37° C. in humidified atmosphere containing 95% air and 5% $CO_2$. As cells become confluent, the cells are detached with 0.25% trypsin with 1 mM EDTA for 5 min at 37° C., and replated at $5 \times 10^3$ cells/$cm^2$. For osteogenic assays, the cells are replated in control medium at $3 \times 10^3$ cells/$cm^2$ in 6 well tissue culture plates. Cells should be approximately 70% confluent. The next day, fresh osteogenic medium is added at two ml per well. The fluid is changed twice a week for approximately 16 days. Morphological changes should be visible after 2-4 days. The cells are then fixed on glass slides for histology staining with 10% formalin.

Verification: The osteogenic differentiation can be verified by the presence of an increase in alkaline phosphatase (using Sigma kit 85) and additionally by the accumulation of calcium, such as by staining with silver by von Kossa method. Additionally, verification using RT-PCR to determine the presence of osteopontin and alkaline phosphatase can be used.

Example 10

Method of Neural Differentiation of MAFSC Cells

The following method was used to demonstrate the differentiation of MAFSC cells to neural cells. The cells were plated on 1 mg/ml poly-d-lysine and 13 µg/ml laminin-coated slides in differentiation medium XXL (DMEM, 15% FCS, pen/strep, 50 ng/ml NGF (nerve growth factor), 20 ng/ml bFGF, 1 mM dibutryl cAMP, 0.5 mM IBMX, 10 µM retinoic acid) for up to 4 weeks. The cells were then stained with anti-GABA, anti-TH and anti-NF cocktail, anti-GFAP, etc. To verify the presence of the neural cells, the cells were stained with anti-huβ-tubulin type III, NSE (Neural-specific enolase).

Example 11

Use of MAFSCs to Promote Bone Marrow Regeneration

MAFSCs can be transplanted into a patient in need of treatment to promote bone marrow regeneration. MAFSC cells of suitable transplantation genotype are differentiated in vitro by state of the art methods into hematopoietic stem and/or progenitor cells, for example by methods similar to those described by Carotta et al., "Directed differentiation and mass cultivation of pure erythroid progenitors from mouse embryonic stem cells", Blood 2004, May 27, prepublished online, DOI 10.1182. MAFSC cells differentiated into specific hematopoietic stem/progenitor cell types can then be used for transplantation to recipients in need of hematopoietic cell transplantation. The generation of multiple MAFSC stem cell lines of different transplantation specificity facilitates the preparation of suitable hematopoietic stem/progenitor cells as a general bone marrow-transplantation resource that possesses minimal transplantation discrepancies for transplantation of patients requiring hematopoietic cell transplantation.

Example 12

Treatment of Diseases Using Transplantation of Differentiated MAFSCs

MAFSCs may be differentiated into tissues such as liver, endocrine, lung, blood cells, neuronal or astroglial cells, which may then be used for transplantation to cure or treat diseases such as cirrhosis of the liver, pancreatitis, diabetes, Parkinson's disease, Alzheimer disease or others. An example for the use of MAFSC cells in blood cell transplantation follows. Non-differentiated MAFSC cells of suitable transplantation genotype are differentiated in vitro by state of the art methods into one or more blood cell types, for example by methods similar to those described by Carotta et al., "Directed differentiation and mass cultivation of pure erythroid progenitors from mouse embryonic stem cells", Blood 2004, May 27, prepublished online, DOI 10.1182. MAFSC cells differentiated into specific blood cell types and/or their progenitors can then be used for transplantation to suitable recipients. The generation of multiple MAFSC stem cell lines of different transplantation specificity facilitates the preparation of suitable blood cell transplantation resources that possess minimal transplantation discrepancies for transplantation of patients requiring such transplantations.

It will be appreciated that no matter how detailed the foregoing appears in text, the invention can be practiced in many ways. As is also stated above, it should further be noted that the use of particular terminology when describing certain features or aspects of the present invention should not be taken to imply that the broadest reasonable meaning of such terminology is not intended, or that the terminology is being re-defined herein to be restricted to including any specific characteristics of the features or aspects of the invention with which that terminology is associated. Thus, although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims and any equivalents thereof. All documents cited herein are incorporated by reference in their entireties.

What is claimed is:

1. A composition comprising isolated, mortal, epithelioid multipotent stem cells derived from amniotic fluid, wherein said stem cells are characterized by expression of SSEA3, SSEA4, Tra1-60, Tra1-81, Tra2-54, Oct-4 and CD105, and by less than 5% expression of SSEA1.

2. The composition of claim 1, wherein the stem cells are characterized by senescence after about 60 population doubling.

3. The composition of claim 1, wherein said cells are derived from a mammal.

4. The composition of claim 3, wherein said mammal is a human.

5. The composition of claim 1, wherein said stem cells are further characterized by expressing the following markers: HLA class I, CD13, CD44, and CD49b.

6. A method of preparing multipotent stem cells, comprising:
   harvesting amniotic fluid;
   centrifuging the amniotic fluid;
   plating cells onto plates coated with fibronectin in medium with 2% serum;
   selecting colonies which adhere to the plates; and
   isolating mortal, epithelioid stem cells.

7. The method of claim 6, further comprising allowing the population of stem cells to proliferate in 2% serum medium.

8. A method of preparing multipotent stem cells, comprising:
   isolating cells from amniotic fluid;
   culturing the cells on plates coated with fibronectin in 2% serum;
   identifying and isolating mortal multipotent epithelioid stem cells based on appearance;
   purifying the stem cells; and
   growing the stem cells in or on a medium.

9. A method of preparing undifferentiated multipotent stem cells, comprising:
   isolating cells from amniotic fluid;
   culturing the cells on plates coated with fibronectin in 2% serum;
   identifying and isolating mortal multipotent epithelioid stem cells based on appearance; and
   expanding the cells in an undifferentiated state.

10. A genetically modified mortal epithelioid stem cell from amniotic fluid wherein said mortal epithelioid stem cell is characterized by expression of SSEA3, SSEA4, Tra1-60, Tra1-81, Tra2-54, Oct-4, and CD105, and by less than 5% expression of SSEA1.

11. The cell of claim 10, which has been genetically modified to express TERT.

12. A multipotent stem cell isolated from amniotic fluid, characterized by a) senescence in about 60 population doublings; b) the presence of SSEA3, Tra1-60, Tra1-81, Tra2-54, Oct-4 and CD105; and c) by less than 5% expression of SSEA1.

* * * * *

UNITED STATES PATENT AND TRADEMARK OFFICE
CERTIFICATE OF CORRECTION

PATENT NO. : 7,569,385 B2 Page 1 of 1
APPLICATION NO. : 10/918739
DATED : August 4, 2009
INVENTOR(S) : Martin Haas It is certified that error appears in the above-identified patent and that said Letters Patent is hereby corrected as shown below:

On Column 5, Lines 60-61, please delete "tumorgenic" and insert --tumorigenic--, therefor.

On Column 11, Line 38, please delete "epihelial" and insert --epithelial--, therefor.

On Column 12, Line 13, please delete "permeablized" and insert --permeabilized--, therefor.

On Column 15, Line 40 (Approx.), please delete "PPAR?2" and insert --PPARγ2--, therefor.

On Column 15, Line 57 (Approx.), please delete "FBS" and insert --FBS.--, therefor.

On Column 17, Line 22 (Approx.), please delete "dibutryl" and insert --dibutyryl--, therefor.

On Column 27, Lines 37-38, in Claim 2, please delete "doubling." and insert --doublings.--, therefor.

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,569,385 B2  Page 1 of 1
APPLICATION NO. : 10/918739
DATED : August 4, 2009
INVENTOR(S) : Martin Haas It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 469 days.

Signed and Sealed this

Seventh Day of September, 2010

David J. Kappos
*Director of the United States Patent and Trademark Office*

SEQUENCE LISTING

```
<160> NUMBER OF SEQ ID NOS: 2

<210> SEQ ID NO 1
<211> LENGTH: 4015
<212> TYPE: DNA
<213> ORGANISM: Homo sapiens

<400> SEQUENCE: 1
gcagcgctgc gtcctgctgc gcacgtggga agccctggcc ccggccaccc ccgcgatgcc      60
gcgcgctccc cgctgccgag ccgtgcgctc cctgctgcgc agccactacc gcgaggtgct     120
gccgctggcc acgttcgtgc ggcgcctggg gccccagggc tggcggctgg tgcagcgcgg     180
ggacccggcg gctttccgcg cgctggtggc ccagtgcctg gtgtgcgtgc cctgggacgc     240
```

-continued

| | |
|---|---|
| acggccgccc cccgccgccc cctccttccg ccaggtgtcc tgcctgaagg agctggtggc | 300 |
| ccgagtgctg cagaggctgt gcgagcgcgg cgcgaagaac gtgctggcct tcggcttcgc | 360 |
| gctgctggac ggggcccgcg ggggcccccc cgaggccttc accaccagcg tgcgcagcta | 420 |
| cctgcccaac acggtgaccg acgcactgcg ggggagcggg gcgtgggggc tgctgctgcg | 480 |
| ccgcgtgggc gacgacgtgc tggttcacct gctggcacgc tgcgcgctct ttgtgctggt | 540 |
| ggctcccagc tgcgcctacc aggtgtgcgg gccgccgctg taccagctcg cgctgccac | 600 |
| tcaggcccgg cccccgccac acgctagtgg accccgaagg cgtctgggat gcgaacgggc | 660 |
| ctggaaccat agccgtcaggg aggccggggt cccctgggc ctgccagccc cgggtgcgag | 720 |
| gaggcgcggg ggcagtgcca gccgaagtct gccgttgccc aagaggccca ggcgtggcgc | 780 |
| tgcccctgag ccgagcgga cgcccgttgg gcaggggtcc tgggcccacc cgggcaggac | 840 |
| gcgtggaccg agtgaccgtg gtttctgtgt ggtgtcacct gccagacccg ccgaagaagc | 900 |
| cacctctttg gagggtgcgc tctctggcac gcgccactcc cacccatccg tgggccgcca | 960 |
| gcaccacgcg ggcccccat ccacatcgcg gccaccacgt ccctgggaca cgccttgtcc | 1020 |
| cccggtgtac gccgagacca agcacttcct ctactcctca ggcgacaagg agcagctgcg | 1080 |
| gccctccttc ctactcagct ctctgaggcc cagcctgact ggcgctcgga ggctcgtgga | 1140 |
| gaccatcttt ctgggttcca ggccctggat gccaggac ccccgcaggt tgccccgcct | 1200 |
| gccccagcgc tactggcaaa tgcggcccct gtttctggag ctgcttggga accacgcgca | 1260 |
| gtgccctac ggggtgctcc tcaagacgca ctgcccgctg cgagctgcgg tcaccccagc | 1320 |
| agccggtgtc tgtgcccggg agaagcccca gggctctgtg gcggccccg aggaggagga | 1380 |
| cacagaccc cgtcgcctgg tgcagctgct ccgccagcac agcagcccct ggcaggtgta | 1440 |
| cggcttcgtg cgggcctgcc tgcgccggct ggtgcccca ggcctctggg gctccaggca | 1500 |
| caacgaacgc cgcttcctca ggaacaccaa gaagttcatc tccctgggga agcatgccaa | 1560 |
| gctctcgctg caggagctga cgtggaagat gagcgtgcgg gactgcgctt ggctgcgcag | 1620 |
| gagcccaggg gttggctgtg ttccggccgc agagcaccgt ctgcgtgagg agatcctggc | 1680 |
| caagttcctg cactggctga tgagtgtgta cgtcgtcgag ctgctcaggt ctttcttta | 1740 |
| tgtcacggag accacgtttc aaaagaacag gctctttttc taccggaaga gtgtctggag | 1800 |
| caagttgcaa agcattggaa tcagacagca cttgaagagg gtgcagctgc gggagctgtc | 1860 |
| ggaagcagag gtcaggcagc atcgggaagc caggcccgcc ctgctgacgt ccagactccg | 1920 |
| cttcatcccc aagcctgacg ggctgcgcc gattgtgaac atggactacg tcgtgggagc | 1980 |
| cagaacgttc cgcagagaaa agagggccga gcgtctcacc tcgagggtga aggcactgtt | 2040 |
| cagcgtgctc aactacgagc gggcgcgcg ccccggcctc ctgggcgcct ctgtgctggg | 2100 |
| cctggacgat atccacaggg cctggcgcac cttcgtgctg cgtgtgcggg cccaggaccc | 2160 |
| gccgcctgag ctgtactttg tcaaggtgga tgtgacgggc gcgtacgaca ccatccccca | 2220 |
| ggacaggctc acggaggtca tcgccagcat catcaaaccc cagaacacgt actgcgtgcg | 2280 |
| tcggtatgcc gtggtccaga aggccgccca tgggcacgtc cgcaaggcct tcaagagcca | 2340 |
| cgtctctacc ttgacagacc tccagccgta catgcgacag ttcgtggctc acctgcagga | 2400 |
| gaccagcccg ctgagggatg ccgtcgtcat cgagcagagc tcctccctga atgaggccag | 2460 |
| cagtggccct ttcgacgtct tcctacgctt catgtgccac cacgccgtgc gcatcagggg | 2520 |
| caagtcctac gtccagtgcc aggggatccc gcagggctcc atcctctcca cgctgctctg | 2580 |
| cagcctgtgc tacggcgaca tggagaacaa gctgtttgcg gggattcggc gggacgggct | 2640 |

```
gctcctgcgt tggtggatg atttcttgtt ggtgacacct cacctcaccc acgcgaaaac    2700
cttcctcagg accctggtcc gaggtgtccc tgagtatggc tgcgtggtga acttgcggaa    2760
gacagtggtg aacttccctg tagaagacga ggccctgggt ggcacggctt ttgttcagat    2820
gccggcccac ggcctattcc cctggtgcgg cctgctgctg atacccggga ccctggaggt    2880
gcagagcgac tactccagct atgcccggac ctccatcaga gccagtctca ccttcaaccg    2940
cggcttcaag gctgggagga acatgcgtcg caaactcttt ggggtcttgc ggctgaagtg    3000
tcacagcctg tttctggatt tgcaggtgaa cagcctccag acggtgtgca ccaacatcta    3060
caagatcctc ctgctgcagg cgtacaggtt tcacgcatgt gtgctgcagc tcccatttca    3120
tcagcaagtt tggaagaacc ccacattttt cctgcgcgtc atctctgaca cggcctccct    3180
ctgctactcc atcctgaaag ccaagaacgc agggatgtcg ctgggggcca agggcgccgc    3240
cggccctctg ccctccgagg ccgtgcagtg gctgtgccac caagcattcc tgctcaagct    3300
gactcgacac cgtgtcacct acgtgccact cctggggtca ctcaggacag cccagacgca    3360
gctgagtcgg aagctcccgg ggacgacgct gactgccctg gaggccgcag ccaacccggc    3420
actgccctca gacttcaaga ccatcctgga ctgatggcca cccgcccaca gccaggccga    3480
gagcagacac cagcagccct gtcacgccgg gctctacgtc ccaggagggg aggggcggcc    3540
cacacccagg cccgcaccgc tgggagtctg aggcctgagt gagtgtttgg ccgaggcctg    3600
catgtccggc tgaaggctga gtgtccggct gaggcctgag cgagtgtcca gccaagggct    3660
gagtgtccag cacacctgcc gtcttcactt ccccacaggc tggcgctcgg ctccacccca    3720
gggccagctt ttcctcacca ggagcccggc ttccactccc cacataggaa tagtccatcc    3780
ccagattcgc cattgttcac ccctcgccct gccctccttt gccttccacc cccaccatcc    3840
aggtggagac cctgagaagg accctgggag ctctgggaat ttggagtgac caaaggtgtg    3900
ccctgtacac aggcgaggac cctgcacctg gatgggggtc cctgtgggtc aaattggggg    3960
gaggtgctgt gggagtaaaa tactgaatat atgagttttt cagttttgaa aaaaa         4015
```

<210> SEQ ID NO 2
<211> LENGTH: 1132
<212> TYPE: PRT
<213> ORGANISM: Homo sapiens

<400> SEQUENCE: 2

```
Met Pro Arg Ala Pro Arg Cys Arg Ala Val Arg Ser Leu Leu Arg Ser
  1               5                  10                  15

His Tyr Arg Glu Val Leu Pro Leu Ala Thr Phe Val Arg Arg Leu Gly
                 20                  25                  30

Pro Gln Gly Trp Arg Leu Val Gln Arg Gly Asp Pro Ala Ala Phe Arg
             35                  40                  45

Ala Leu Val Ala Gln Cys Leu Val Cys Val Pro Trp Asp Ala Arg Pro
         50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
                100                 105                 110

Glu Ala Phe Thr Thr Ser Val Arg Ser Tyr Leu Pro Asn Thr Val Thr
            115                 120                 125
```

-continued

```
Asp Ala Leu Arg Gly Ser Gly Ala Trp Gly Leu Leu Leu Arg Arg Val
            130                 135                 140
Gly Asp Asp Val Leu Val His Leu Leu Ala Arg Cys Ala Leu Phe Val
145                 150                 155                 160
Leu Val Ala Pro Ser Cys Ala Tyr Gln Val Cys Gly Pro Pro Leu Tyr
                165                 170                 175
Gln Leu Gly Ala Ala Thr Gln Ala Arg Pro Pro His Ala Ser Gly
            180                 185                 190
Pro Arg Arg Arg Leu Gly Cys Glu Arg Ala Trp Asn His Ser Val Arg
            195                 200                 205
Glu Ala Gly Val Pro Leu Gly Leu Pro Ala Pro Gly Ala Arg Arg Arg
    210                 215                 220
Gly Gly Ser Ala Ser Arg Ser Leu Pro Leu Pro Lys Arg Pro Arg Arg
225                 230                 235                 240
Gly Ala Ala Pro Glu Pro Glu Arg Thr Pro Val Gly Gln Gly Ser Trp
                245                 250                 255
Ala His Pro Gly Arg Thr Arg Gly Pro Ser Asp Arg Gly Phe Cys Val
            260                 265                 270
Val Ser Pro Ala Arg Pro Ala Glu Glu Ala Thr Ser Leu Glu Gly Ala
            275                 280                 285
Leu Ser Gly Thr Arg His Ser His Pro Ser Val Gly Arg Gln His His
    290                 295                 300
Ala Gly Pro Pro Ser Thr Ser Arg Pro Arg Pro Trp Asp Thr Pro
305                 310                 315                 320
Cys Pro Pro Val Tyr Ala Glu Thr Lys His Phe Leu Tyr Ser Ser Gly
                325                 330                 335
Asp Lys Glu Gln Leu Arg Pro Ser Phe Leu Leu Ser Ser Leu Arg Pro
            340                 345                 350
Ser Leu Thr Gly Ala Arg Arg Leu Val Glu Thr Ile Phe Leu Gly Ser
    355                 360                 365
Arg Pro Trp Met Pro Gly Thr Pro Arg Arg Leu Pro Arg Leu Pro Gln
    370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
            420                 425                 430
Gly Ser Val Ala Ala Pro Glu Glu Asp Thr Asp Pro Arg Arg Leu
    435                 440                 445
Val Gln Leu Leu Arg Gln His Ser Ser Pro Trp Gln Val Tyr Gly Phe
    450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Gln Glu Leu Thr Trp Lys Met
            500                 505                 510
Ser Val Arg Asp Cys Ala Trp Leu Arg Arg Ser Pro Gly Val Gly Cys
            515                 520                 525
Val Pro Ala Ala Glu His Arg Leu Arg Glu Glu Ile Leu Ala Lys Phe
    530                 535                 540
Leu His Trp Leu Met Ser Val Tyr Val Val Glu Leu Leu Arg Ser Phe
```

-continued

```
            545                 550                 555                 560
        Phe Tyr Val Thr Glu Thr Thr Phe Gln Lys Asn Arg Leu Phe Phe Tyr
                        565                 570                 575

Arg Lys Ser Val Trp Ser Lys Leu Gln Ser Ile Gly Ile Arg Gln His
                        580                 585                 590

Leu Lys Arg Val Gln Leu Arg Glu Leu Ser Glu Ala Glu Val Arg Gln
                        595                 600                 605

His Arg Glu Ala Arg Pro Ala Leu Leu Thr Ser Arg Leu Arg Phe Ile
                        610                 615                 620

Pro Lys Pro Asp Gly Leu Arg Pro Ile Val Asn Met Asp Tyr Val Val
        625                 630                 635                 640

Gly Ala Arg Thr Phe Arg Arg Glu Lys Arg Ala Glu Arg Leu Thr Ser
                        645                 650                 655

Arg Val Lys Ala Leu Phe Ser Val Leu Asn Tyr Glu Arg Ala Arg Arg
                        660                 665                 670

Pro Gly Leu Leu Gly Ala Ser Val Leu Gly Leu Asp Asp Ile His Arg
                        675                 680                 685

Ala Trp Arg Thr Phe Val Leu Arg Val Arg Ala Gln Asp Pro Pro
                        690                 695                 700

Glu Leu Tyr Phe Val Lys Val Asp Val Thr Gly Ala Tyr Asp Thr Ile
        705                 710                 715                 720

Pro Gln Asp Arg Leu Thr Glu Val Ile Ala Ser Ile Ile Lys Pro Gln
                        725                 730                 735

Asn Thr Tyr Cys Val Arg Arg Tyr Ala Val Val Gln Lys Ala Ala His
                        740                 745                 750

Gly His Val Arg Lys Ala Phe Lys Ser His Val Ser Thr Leu Thr Asp
                        755                 760                 765

Leu Gln Pro Tyr Met Arg Gln Phe Val Ala His Leu Gln Glu Thr Ser
                        770                 775                 780

Pro Leu Arg Asp Ala Val Val Ile Glu Gln Ser Ser Ser Leu Asn Glu
        785                 790                 795                 800

Ala Ser Ser Gly Leu Phe Asp Val Phe Leu Arg Phe Met Cys His His
                        805                 810                 815

Ala Val Arg Ile Arg Gly Lys Ser Tyr Val Gln Cys Gln Gly Ile Pro
                        820                 825                 830

Gln Gly Ser Ile Leu Ser Thr Leu Leu Cys Ser Leu Cys Tyr Gly Asp
                        835                 840                 845

Met Glu Asn Lys Leu Phe Ala Gly Ile Arg Arg Asp Gly Leu Leu Leu
                        850                 855                 860

Arg Leu Val Asp Asp Phe Leu Leu Val Thr Pro His Leu Thr His Ala
        865                 870                 875                 880

Lys Thr Phe Leu Arg Thr Leu Val Arg Gly Val Pro Glu Tyr Gly Cys
                        885                 890                 895

Val Val Asn Leu Arg Lys Thr Val Val Asn Phe Pro Val Glu Asp Glu
                        900                 905                 910

Ala Leu Gly Gly Thr Ala Phe Val Gln Met Pro Ala His Gly Leu Phe
                        915                 920                 925

Pro Trp Cys Gly Leu Leu Leu Asp Thr Arg Thr Leu Glu Val Gln Ser
                        930                 935                 940

Asp Tyr Ser Ser Tyr Ala Arg Thr Ser Ile Arg Ala Ser Leu Thr Phe
        945                 950                 955                 960

Asn Arg Gly Phe Lys Ala Gly Arg Asn Met Arg Arg Lys Leu Phe Gly
                        965                 970                 975
```

-continued

```
Val Leu Arg Leu Lys Cys His Ser Leu Phe Leu Asp Leu Gln Val Asn
            980             985             990

Ser Leu Gln Thr Val Cys Thr Asn Ile Tyr Lys Ile Leu Leu Leu Gln
            995            1000            1005

Ala Tyr Arg Phe His Ala Cys Val Leu Gln Leu Pro Phe His Gln Gln
           1010            1015            1020

Val Trp Lys Asn Pro Thr Phe Phe Leu Arg Val Ile Ser Asp Thr Ala
1025                1030            1035            1040

Ser Leu Cys Tyr Ser Ile Leu Lys Ala Lys Asn Ala Gly Met Ser Leu
           1045            1050            1055

Gly Ala Lys Gly Ala Ala Gly Pro Leu Pro Ser Glu Ala Val Gln Trp
           1060            1065            1070

Leu Cys His Gln Ala Phe Leu Leu Lys Leu Thr Arg His Arg Val Thr
           1075            1080            1085

Tyr Val Pro Leu Leu Gly Ser Leu Arg Thr Ala Gln Thr Gln Leu Ser
           1090            1095            1100

Arg Lys Leu Pro Gly Thr Thr Leu Thr Ala Leu Glu Ala Ala Ala Asn
1105                1110            1115            1120

Pro Ala Leu Pro Ser Asp Phe Lys Thr Ile Leu Asp
               1125            1130
```